United States Patent [19]

Martel et al.

[11] Patent Number: 4,808,749

[45] Date of Patent: Feb. 28, 1989

[54] CYCLOPROPANE CARBOXYLIC ESTERS AND ACIDS

[75] Inventors: Jacques Martel, Bondy; Jean Tessier, Vincennes; André Tèche, Paris, all of France

[73] Assignee: Roussel Uclaf, Paris, France

[21] Appl. No.: 932,179

[22] Filed: Nov. 18, 1986

Related U.S. Application Data

[60] Continuation of Ser. No. 756,374, Jul. 18, 1985, abandoned, which is a division of Ser. No. 655,202, Sep. 26, 1984, abandoned, which is a division of Ser. No. 495,481, May 17, 1983, Pat. No. 4,489,093, which is a continuation-in-part of Ser. No. 306,780, Sep. 29, 1981, abandoned.

[30] Foreign Application Priority Data

Oct. 1, 1980 [FR] France .................. 80-21017
Nov. 22, 1982 [FR] France .................. 82-19516

[51] Int. Cl.$^4$ .................. C07C 121/46; C07C 53/134
[52] U.S. Cl. .................. 558/434; 560/124
[58] Field of Search .................. 560/124; 546/302; 548/204, 312; 549/417, 500; 558/467, 434

[56] References Cited

U.S. PATENT DOCUMENTS 4,489,093  12/1984  Martel et al. .................. 558/432

Primary Examiner—Anton H. Sutto
Attorney, Agent, or Firm—Bierman and Muserlian

[57] ABSTRACT

Novel esters in all possible isomeric forms of the formula

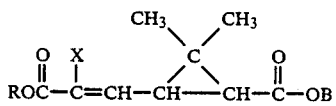

wherein R is selected from the group consisting of (a) optionally unsaturated alkyl of 1 to 8 carbon atoms and optionally unsaturated cycloalkyl or cycloalkyl-alkyl of 3 to 8 carbon atoms optionally substituted with at least one member of the group consisting of halogen, —OH, —SH, —OR', —SR', —NO$_2$,

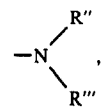

—CN, —SO$_3$H, —PO$_4$H$_2$,

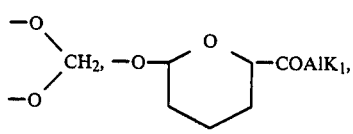

—SO$_2$AlK$_2$, —SO$_3$AlK$_3$, aryl optionally substituted with at least one member of the group consisting of —OH, alkoxy of 1 to 8 carbon atoms, alkyl of 1 to 8 carbon atoms, halogen, —CF$_3$, —OCF$_3$, —SCF$_3$ and

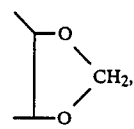

R' is alkyl of 1 to 8 carbon atoms, R" and R'" are individually selected from the group consisting of hydrogen and alkyl of 1 to 8 carbon atoms, AlK$_1$, AlK$_2$ and AlK$_3$ are individually alkyl of 1 to 18 carbon atoms, (b) aryl of 6 to 14 carbon atoms optionally substituted with at least one substitutent selected from the group consisting of —OH, alkoxy of 1 to 8 carbon atoms, alkyl of 1 to 8 carbon atoms, halogen, —OCF$_3$, —CF$_3$ and —SCF$_3$ and (c) heterocycle optionally substituted with at least one member of the group consisting of —OH, alkoxy of 1 to 8 carbon atoms, alkyl of 1 to 8 carbon atoms, halogen, —CF$_3$, —OCF$_3$ and —SCF$_3$, B is selected from the group consisting of optionally unsaturated alkyl of 1 to 18 carbon atoms, optionally unsaturated cycloalkyl of 3 to 18 carbon atoms and the remainder of an alcohol used in synthesis of pyrethrinoid esters, X is halogen and the ethylenic double bond may have Z or E geometry having parasitic activity, especially insecticidal acaricidal and nematocidal activity.

2 Claims, No Drawings

CYCLOPROPANE CARBOXYLIC ESTERS AND ACIDS

PRIOR APPLICATION

This application is a continuation of U.S. patent application Ser. No. 756,374 field July 18, 1985, now abandoned which is a division of U.S. patent application Ser. No. 655,202 filed Sept. 26, 1984, now abandoned which in turn is a division of U.S. patent application Ser. No. 495,481 filed May 17, 1983, now U.S. Pat. No. 4,489,093 which in turn is a continuation-in-part of our copending, commonly assigned U.S. patent application Ser. No. 306,780 filed Sept. 29, 1981 now abandoned.

STATE OF THE ART

Certain derivatives of cyclopropane carboxylic acid derivatives are known having in the 3-position the group ROOC—CH=CH— having essentially E geometry. Examples of such prior art are French Pat. No. 2,185,612 as well as J. Chem. Soc., Perkin I (1974), p. 2470 and Pest. Sci., Vol. 7 (1976), p. 499. The processes used to prepare these derivatives leads almost exclusively to the E geometry (for example Arg. Biol. Chem. Vol. 34 (1970), p. 1119). Furthermore, for those compounds with the side chain geometry in the E state, it has not been possible to make evident any remarkable properties. The French Pat. Nos. 2,418,218 and 2,143,820 also describe compounds substituted in the 3-position by the group ROOC—CH=CH—.

OBJECTS OF THE INVENTION

It is an object of the invention to provide the novel Z and E isomers of the compounds of formula I as well as a novel process and novel intermediates for their preparation.

It is another object of the invention to provide novel pesticidal compositions and a novel method of killing insects and acariens.

It is a further object of the invention to provide novel compositions and method of combatting scabies and to provide anthelmintic activity.

These and other objects and advantages of the invention will become obvious from the following detailed description.

THE INVENTION

The novel compounds of the invention are esters in all possible isomeric forms of the formula

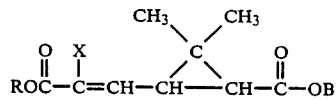

wherein R is selected from the group consisting of (a) optionally unsaturated alkyl of 1 to 8 carbon atoms and optionally unsaturated cycloalkyl or cycloalkyl-alkyl of 3 to 8 carbon atoms optionally substituted with at least one member of the group consisting of halogen, —OH, —SH, —OR', —SR', —NO$_2$,

—CN, —SO$_3$H, —PO$_4$H$_2$,

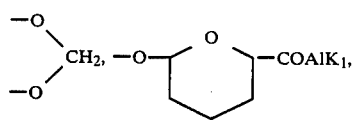

—SO$_2$AlK$_2$, —SO$_3$AlK$_3$, aryl optionally substituted with at least one member of the group consisting of —OH, alkoxy of 1 to 8 carbon atoms, alkyl of 1 to 8 carbon atoms, halogen, —CF$_3$, —OCF$_3$, —SCF$_3$ and

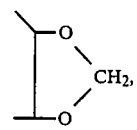

R' is alkyl of 1 to 8 carbon atoms, R" and R''' are individually selected from the group consisting of hydrogen and alkyl of 1 to 8 carbon atoms, AlK$_1$, AlK$_2$ and AlK$_3$ are individually alkyl of 1 to 8 carbon atoms, (b) aryl of 6 to 14 carbon atoms optionally substituted with at least one substitutent selected from the group consisting of —OH, alkoxy of 1 to 8 carbon atoms, alkyl of 1 to 8 carbon atoms, halogen, —OCF$_3$, —CF$_3$ and —SCF$_3$ and (c) heterocycle optionally substituted with at least one member of the group consisting of —OH alkoxy of 1 to 8 carbon atoms, alkyl of 1 to 8 carbon atoms, halogen, —CF$_3$, —OCF$_3$ and —SCF$_3$, B is selected from the group consisting of optionally unsaturated alkyl of 1 to 18 carbon atoms, optionally unsaturated cycloalkyl of 3 to 18 carbon atoms and the remainder of an alcohol used in synthesis of pyrethrinoid esters, X is halogen and the ethylenic double bond may have Z or E geometry.

The compounds of formula I exist in isomeric forms due to the presence of asymmetric carbon atoms in the 1- and 3-positions of the ring, to other asymmetric centers in the alcohol portions thereof and to the configuration of the double bond in the side chain in the 3-position.

Examples of B are alkyl such as methyl, ethyl, n-propyl, isopropyl, isobutyl, tert.-butyl and n-butyl or the remainder of an alcohol used in the synthesis of pesticidal esters of the pyrethrinoid series, preferably one of the list of radicals listed infra.

When R is a saturated alkyl, it is preferably methyl, ethyl, isopropyl, n-propyl, n-butyl, sec.-butyl, isobutyl, n-pentyl, n-hexyl, tert.-butyl, tert.-pentyl or neopentyl. When R is cycloalkyl, it is preferably cyclopropyl, cyclobutyl, cyclopentyl or cyclohexyl. When R is cycloalkyl-alkyl, it is preferably one of these above saturated alkyls substituted by cyclopropyl, cyclobutyl, cyclopentyl or cyclohexyl. The cycloalkyls or cycloalkyl-alkyls can be optionally substituted with at least one alkyl in which the bond with the —COO— group is situated at any of its points such as 1-methylcyclobutyl, 1-methyl-cyclopentyl, 1-methylcyclohexyl and 2,2,3,3-tetramethylcyclopropyl. When R is an unsaturated alkyl, it can have an ethylenic bond such as vinyl or 1,1-dimethylallyl or an acetylenic bond such as ethynyl or propynyl.

Examples of R as alkyl substituted with one or more functional groups are preferably alkyl of 1 to 8 carbon atoms such as methyl, ethyl, propyl, isopropyl, n-butyl, isobutyl or tert.-butyl substituted with at least one member of the group consisting of halogen, —OH, —SH, —OR' and —SR' and R' is selected from the group consisting of alkyl of 1 to 8 carbon atoms, —NO$_2$, —CN, —SO$_3$H, —PO$_4$H$_2$,

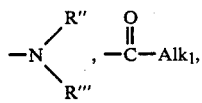 (Alk$_1$)

—SO$_2$AlK$_2$ and —SO$_3$AlK$_3$, R" and R'" are individually selected from the group consisting of hydrogen and alkyl of 1 to 8 carbon atoms and AlK$_1$, AlK$_2$ and AlK$_3$ are alkyl of 1 to 18 carbon atoms.

R may also be alkyl substituted with an aryl group such as benzyl or phenethyl optionally substituted with at leadt one member of the group consisting of —OH, alkyl and alkoxy of 1 to 8 carbon atoms, halogen, —CF$_3$, —OCF$_3$ —SCF$_3$ and

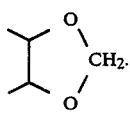 (G)

R may also be alkyl substituted on two adjacent carbon atoms with the group

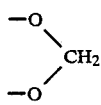

(G$_1$) or substituted with

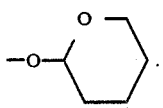

When R is alkyl radical substituted by one or more functional groups, the preferred examples of R are (1) —(CH$_2$)$_n$—CHal$_3$ wherein n is an integer from 1 to 8 and Hal is a halogen, such as —CH$_2$—CCl$_3$, —CH$_2$—CF$_3$, —CH$_2$—CH$_2$—CCl$_3$ or —CH$_2$—CH$_2$—CF$_3$, (2) —(CH$_2$)$_{n_1}$—CHHal$_2$ wherein $n_1$ is 0 to 8 and Hal is halogen such as —CH$_2$—CHCl$_2$, —CH$_2$—CHF$_2$ and —CHF$_2$, (3) —(CH$_2$)$_n$—CH$_2$Hal wherein Hal and n have the above definitions, such as —CH$_2$—CH$_2$—Cl or —CH$_2$—CH$_2$F, (4) —C—(CHal$_3$)$_3$ wherein Hal is a halogen, such as —C(CF$_3$)$_3$ or

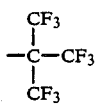

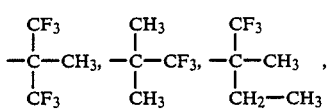 (5)

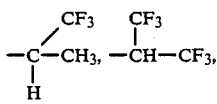 (6)

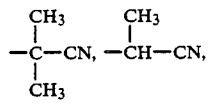 (7)

—(CH$_2$)$_n$—CN wherein n is 1 to 8,

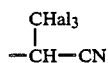 (8)

wherein Hal is halogen, such as

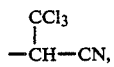

(CH$_2$)$_n$—OR' wherein n has the above definition and R' is hydrogen or branched or linear alkyl of 1 to 8 carbon atoms such as —CH$_2$—OCH$_3$, —CH$_2$—CH$_2$—OCH$_3$, —CH$_2$—CH$_2$—O—CH$_2$—CH$_3$ or —CH$_2$—CH$_2$—OH,

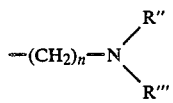 (10)

wherein n is 1 to 8 and R" and R'" are individually hydrogen or branched or linear alkyl such as —CH$_2$—CH$_2$—NH—CH$_3$,

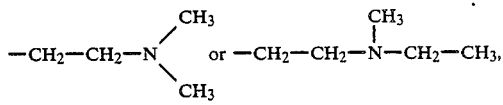

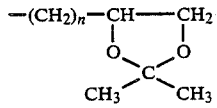 (11)

wherein n is 1 to 8 such as

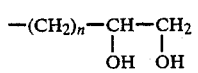

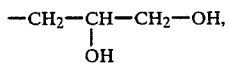 (12)

wherein n is 1 to 8 such as

—CH$_2$—CH—CH$_2$—OH,
      |
      OH

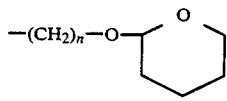

wherein n is 1 to 8 such as

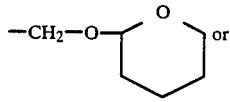

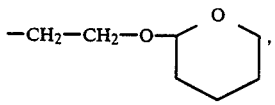

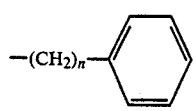

wherein n is 1 to 8 such as benzyl or phenethyl and

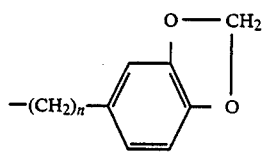

wherein n is 1 to 8 such as

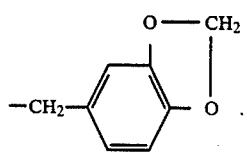

When R is an optionally substituted aryl, preferred examples are phenyl optionally substituted with at least one member of the group consisting of —OH, alkyl and alkoxy of 1 to 8 carbon atoms, halogen, —CF$_3$, —OCF$_3$ and —SCF$_3$. Examples of R as heterocycles are [pyridinyl, furanyl, thiophenyl, oxazolyl and thiazolyl]. The preferred halogens are fluorine, chlorine or bromine.

Among the compounds of the invention, the preferred compounds are those wherein the moiety of cyclopropanic acid have 1R cis or 1R trans configuration.

Among the compounds of the invention, the preferred compounds have a double bond with the E geometry and among the preferred compounds are those wherein X is fluorine, those wherein R is alkyl of 1 to 8 carbon atoms or cycloalkyl of 3 to 8 carbon atoms, especially ethyl, tert-butyl, cyclopropyl or cyclopropylmethyl, those wherein R is alkyl of 1 to 8 carbon atoms substituted with at least one halogen atom such as fluorine and those wherein R is —(CH$_2$)$_m$—O—(CH$_2$)$_n$—CH$_3$ wherein m is an integer from 1 to 8 and n is an integer from 0 to 8, especially —CH$_2$—OCH$_3$.

Among the preferred compounds of formula I are those wherein B is selected from the group consisting of (1) alkyl of 1 to 18 carbon atoms, (2) benzyl optionally substituted with at least one member of the group consisting of alkyl of 1 to 4 carbon atoms, alkenyl of 2 to 6 carbon atoms, alkenyloxy of 2 to 6 carbon atoms, alkadienyl of 4 to 8 carbon atoms, methylenedioxy and halogens,

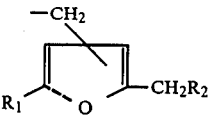

wherein R$_1$ is selected from the group consisting of hydrogen and methyl and R$_2$ is selected from the group consisting of —CH$_2$—C≡CH and monocyclic aryl,

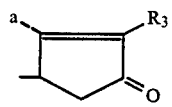

wherein a is selected from the group consisting of hydrogen and methyl and R$_3$ is an aliphatic group of 2 to 6 carbon atoms containing at least one carbon-carbon unsaturation,

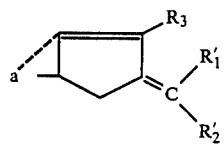

wherein a and R$_3$ have the above definition and R$_1$' and R$_2$' are individually selected from the group consisting of hydrogen, halogen, alkyl of 1 to 6 carbon atoms, aryl of 6 to 10 carbon atoms, cyano and alkoxy carbonyl of 2 to 5 carbon atoms,

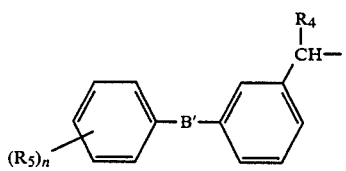

wherein B' is selected from the group consisting of

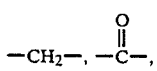

—O—, —S—, —SO— and —SO$_2$—, R$_4$ is selected from the group consisting of hydrogen, C≡N, —CH$_3$, —CONH$_2$, —CSNH$_2$ and —C≡CH, n is an integer from 0, 1 or 2 and R$_5$ is selected from the group consisting of halogen and —CH$_3$ (7)

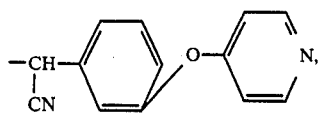

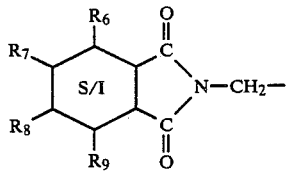 (8)

wherein $R_6$, $R_7$, $R_8$ and $R_9$ are selected from the group consisting of hydrogen, chlorine and methyl and S/I symbolizes an aromatic ring or dihydro or tetrahydro ring

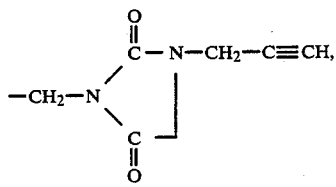 (9)

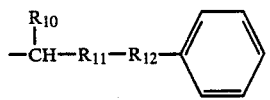 (10)

wherein $R_{10}$ is selected from the group consisting of hydrogen and —CN, $R_{12}$ is selected from the group consisting of —CH$_2$— and —O— and $R_{11}$ is selected from the group consisting of thiazolyl and thiadiazolyl with the bond to —CH$^{10}$— being in any one of the positions, $R_{12}$ being bonded to $R_{11}$ by the carbon atom included between a sulfur atom and a nitrogen atom,

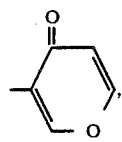 (11)

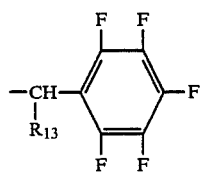 (12)

wherein $R_{13}$ is selected from the group consisting of hydrogen and —CN,

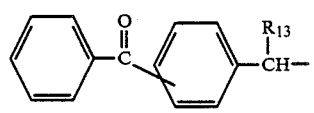 (13)

wherein $R_{13}$ has the above definition and the benzoyl is in the 3- or 4-position,

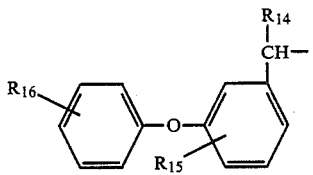 (14)

wherein $R_{14}$ is selected from the group consisting of hydrogen, methyl, ethynyl and —CN and $R_{15}$ and $R_{16}$ are individually selected from the group consisting of hydrogen, bromine and fluorine and (15)

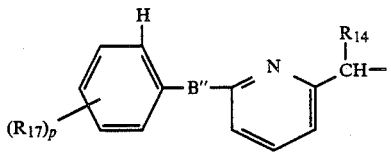

wherein $R_{14}$ has the above definition, p is 0, 1 or 2, each $R_{17}$ is selected from the group consisting of alkyl of 1 to 4 carbon atoms, alkoxy of 1 to 4 carbon atoms, alkylthio of 1 to 4 carbon atoms, alkylsulfonyl of 1 to 4 carbon atoms, —CF$_3$, 3,4-methylenedioxy, chlorine, bromine fluorine, B″ is selected from the group consisting of —O— and —S—.

An example of $R_2$ as monocyclic aryl is 5-benzyl-3-furyl-methyl and examples of $R_3$ are —CH$_2$—CH=CH$_2$, —CH$_2$—CH=CH—CH$_3$, —CH$_2$—CH=CH—CH$_2$—CH$_3$ and —CH$_2$—CH=CH—CH=CH$_2$. Examples of substituent (6) are 3-phenoxy-benzyl; α-cyano-3-phenoxy-benzyl, α-ethynyl-3-phenoxy-benzyl, 3-benzoyl-benzyl, 1-(3-phenoxyphenyl)-ethyl and α-thioamido-3-phenoxy benzyl.

When B is benzyl substituted with at least one alkyl, the alkyls are preferably methyl or ethyl and when B is benzyl substituted with at least one alkenyl, the alkenyl is preferably vinyl, allyl, 2-methylallyl or isobutenyl. When B is benzyl substituted with alkadienyl, the alkadienyl preferably contains 4, 5 or 6 carbon atoms. When B is benzyl substituted with at least one alkenyloxy, it is preferably vinyloxy, allyloxy, 2-methylallyloxy or isobutenyloxy. When B is benzyl substituted with at least one halogen, the halogens are preferably fluorine, chlorine or bromine.

When B is

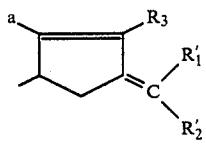

$R_3$ is preferably —CH$_2$—CH=CH$_2$, —CH$_2$—CH=CH—CH$_3$, —CH$_2$—CH=CH—CH=CH$_2$ or —CH$_2$—CH=CH—CH$_2$—CH$_3$, $R_1'$ and/or $R_2'$ are preferably chlorine, bromine or fluorine, alkyl such as methyl, ethyl, n-propyl or n-butyl, aryl such as phenyl and/or alkoxycarbonyl such as methoxycarbonyl or ethoxycarbonyl.

When B is

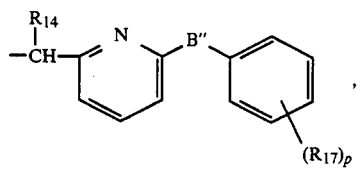

$R_{17}$ is preferably alkyl, alkoxy, alkylthio or alkylsulfonyl such as methyl, ethyl, methoxy, ethoxy, methylthio, ethylthio, methylsulfonyl or ethylsulfonyl.

Among the preferred compounds of the invention are those of the formula

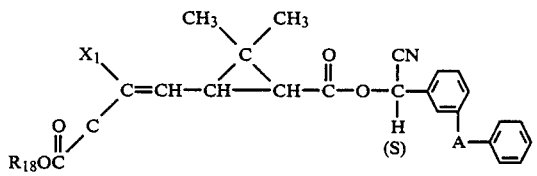

wherein A is selected from the group consisting of —O—, —S—, —CH$_2$—,

—SO— and —SO$_2$— R$_{18}$ is alkyl of 1 to 8 carbon atoms X$_1$ is selected from the group consisting of fluorine, chlorine and bromine and the double bond has the (E) or (Z) geometry and the substituted cyclopropane ring may be in any one of its stereoisomeric forms or mixtures thereof.

Among the preferred compounds of formula I$_4$, R$_{18}$ is alkyl such as methyl, ethyl, isopropyl, n-propyl and linear or branched butyl, pentyl, hexyl, heptyl or octyl and the cyclopropane ring may have the (1R,cis), (1S,cis), (1R,trans) or (1S,trans) configuration, but is preferably (1R,cis) or (1R,trans) and A is preferably oxygen.

An especially preferred compound of the invention is (S)α-cyano-3-phenoxy-benzyl (1R,cis) 2,2-dimethyl-3(E)-[2-fluoro-3-oxo-3-ethoxy-propenyl]-cyclopropane-1-carboxylate and the compounds of Examples 11 and 21.

Among the preferred compounds of the invention are those wherein B is

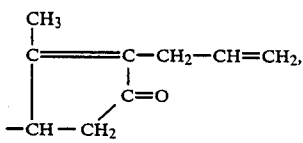

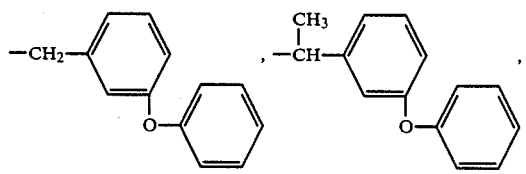

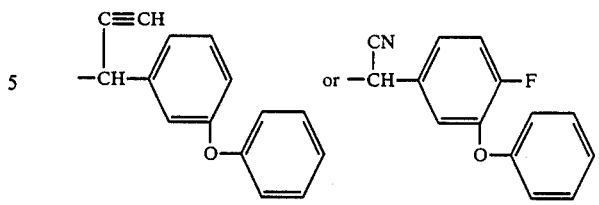

B is preferably α-cyano-6-phenoxy-2-pyridyl-methyl or [3-(propyn-2-yl)-2,5-dioxo-imidazolidinyl]-methyl.

Other specific preferred compounds of the invention are 3-phenoxy-benzyl (1R,cis,E) 2,2-dimethyl-3-[2-fluoro-3-oxo-3-(1,1-dimethylethoxy)-1-propenyl]-cyclopropanecarboxylate, (R)2-methyl-3-phenoxy-benzyl (1R,cis,E) 2,2-dimethyl-3-[2-fluoro-3-oxo-3-(1,1-dimethylethoxy)-1-propenyl]-cyclopropanecarboxylate, (R)α-ethynyl-3-phenoxy-benzyl (1R,cis,E) 2,2-dimethyl-3-[2-fluoro-3-oxo-3-(1,1-dimethylethoxy)-1-propenyl]-cyclopropanecarboxylate, (S)α-cyano-3-phenoxy-4-fluoro-benzyl (1R,cis,E) 2,2-dimethyl-3-[2-chloro-3-oxo-3-(1,1-dimethylethoxy)-1-propenyl]-cyclopropanecarboxylate, (S)α-cyano-3-phenoxy-benzyl (1R,cis,Z) 2,2-dimethyl-3-[2-chloro-3-oxo-3-(1,1-dimethylethoxy)-1-propenyl]-cyclopropanecarboxylate, (S)α-cyano-3-phenoxy-4-fluoro-benzyl (1R,cis,E) 2,2-dimethyl-3-[2-fluoro-3-oxo-methoxy-1-propenyl]-cyclopropanecarboxylate, (S)2-methyl-3-[2-propen-1-yl]-4-oxo-2-cyclopenten-1-yl (1R,cis,E) 2,2-dimethyl-3-[2-fluoro-3-oxo-3-methoxy-1-propenyl]-cyclopropanecarboxylate, (S)α-cyano-3-phenoxy-4-fluoro-benzyl (1R,cis,E) 2,2-dimethyl-3-[2-fluoro-3-oxo-3-(1,1-dimethyethoxy)-1-propenyl]-cyclopropanecarboxylate, (S)α-cyano-3-phenoxy-benzyl (1R,cis,E) 2,2-dimethyl-3-[2-fluoro-3-oxo-3-(2,2,2-trifluoroethoxy)-1-propenyl]-cyclopropanecarboxylate, (S)α-cyano-3-phenoxy-benzyl (1R,cis,Z) 2,2-dimethyl-3-[2-bromo-3-oxo-3-ethoxy-1-propenyl]-cyclopropanecarboxylate, the E and Z isomers of (S)α-cyano-3-phenoxy-benzyl (1R,cis) 2,2-dimethyl-3-[2-chloro-3-oxo-3-(1-methyl-propoxy)-1-propenyl]-cyclopropanecarboxylate, the E and Z isomers of (S)α-cyano-3-phenoxy-benzyl (1R,cis) 2,2-dimethyl-3-[2-bromo-3-oxo-3-(1-methylpropoxy)-1-propenyl]-cyclopropanecarboxylate, (S)α-cyano-3-phenoxy-4-fluorobenzyl (1R,cis,E) 2,2-dimethyl-3-[2-fluoro-3-oxo-3-(2,2,2-trifluoroethoxy)-1-propenyl]-cyclopropanecarboxylate, [3-(2-propyn-1-yl)-2,5-dioxo-1-imidazolidin-yl]-methyl (1R,cis,Z) 2,2-dimethyl-3-[2-fluoro-3-oxo-3-ethoxy-1-propenyl]-cyclopropanecarboxylate, (S)[2-methyl-3-(2-propen-1-yl-4-oxo-2-cyclopenten-1-yl) (1R,cis,Z) 2,2-dimethyl-3-[2-fluoro-3-oxo-3-ethoxy-1-propenyl]-cyclopropanecarboxylate, the E and Z isomers of (S)α-cyano-3-phenoxy-benzyl (1R,trans) 2,2-dimethyl-3-[2-bromo-3-oxo-3-ethoxy-1-propenyl]-cyclopropanecarboxylate, [3-(2-propyn-1-yl)-2,5-dioxo-1-imidazolidinyl]-methyl (1R,cis,E) 2,2-dimethyl-3-[2-fluoro-3-oxo-3-methoxy-1-propenyl]-cyclopropane carboxylate, the E and Z isomers of benzyl (1R,cis) 2,2-dimethyl-3-[2-fluoro-3-oxo-3-ethoxy-1-propenyl]-cyclopropanecarboxylate, pentafluorobenzyl (1R,cis,E) 2,2-dimethyl-3-[2-fluoro-3-oxo-3-ethoxy-1-propenyl]-cyclopropanecarboxylate, the E and Z isomers of 4-fluoro-benzyl (1R,cis) 2,2-dimethyl-3-[2-fluoro-3-oxo-3-ethoxy-1-propenyl]-cyclopropanecarboxylate, the E and Z isomers of pentafluorobenzyl (1R,cis) 2,2-dimethyl-3-[2-fluoro-3-oxo-3-(1,1-dimethylethoxy)-1-propenyl]-cyclopropanecarboxylate, the E and Z isomers of benzyl (1R,cis) 2,2-dimethyl-3-[2-fluoro-3-oxo-3-(1,1-dimethylethoxy)-1-propenyl]-cyclopropanecarboxylate, pentafluorobenzyl (1R,cis,E) 2,2-dimethyl-3-[2-fluoro-3-oxo-3-methoxy-1-propenyl]-cyclopropanecarboxylate, α-cyano-benzyl-(1R,cis,E) 2,2-dimethyl-3-[2-fluoro-3-oxo-3-ethoxy-1-propenyl]-cyclopropanecarboxylate, benzyl (1R,cis,E) 2,2-dimethyl-3-[2-fluoro-3-oxo-3-methoxy-1-propenyl]-cyclopropanecarboxylate, benzyl (1R,cis,E) 2,2-dimethyl-3-[2-fluoro-3-oxo-3-ethenyloxy-1-propenyl]-cyclopropanecarboxylate, the Z and E isomers of 4-nitro-benzyl (1R,cis) 2,2-dimethyl-3-[2-fluoro-3-oxo-3-ethoxy-1-propenyl]-cyclopropanecarboxylate, the E and Z isomers of α-phenylethyl (1R,cis) 2,2-dimethyl-3-[2-fluoro-3-oxo-3-ethoxy-1-propenyl]-cyclopropanecarboxylate, α-ethynylbenzyl (1R,cis,E) 2,2-dimethyl-3-[2-fluoro-3-oxo-3-ethoxy-1-propenyl]-cyclopropanecarboxylate, benzyl (1R,cis,E) 2,2-dimethyl-3-[2-fluoro-3-oxo-3-(1,1-ditrifluoromethylmethoxy)-1-propenyl]-cyclopropanecarboxylate, benzyl (1R,cis,E) 2,2-dimethyl-3-[2-fluoro-3-oxo-3-(2,2,2-trifluoroethoxy)-1-propenyl]-cyclopropanecarboxylate, benzyl (1R,cis,E) 2,2-dimethyl-3-[2-fluoro-3-oxo-3-(2,2-difluoroethoxy)-1-propenyl]cyclopropanecarboxylate, benzyl (1R,cis,E) 2,2-dimethyl-3-[2-fluoro-3-oxo-3-(2-fluoroethoxy)-1-propenyl]-cyclopropanecarboxylate and pentafluorobenzyl (1R,cis,Z) 2,2-dimethyl-3-[2-fluoro-3-oxo-3-ethoxy-1-propenyl]cyclopropanecarboxylate.

The novel process of the invention for the preparation of the compounds of formula I comprises reacting a compound of the formula

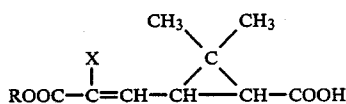

II wherein R and X have the above definitions in the form of a mixture of its (E) and (Z) isomers or in the (E) form or (Z) form, the acid cyclopropanic moiety being in all its stereoisomeric forms or mixtures thereof or a functional derivative thereof with an alcohol of the formula

 III wherein B has the above definition to obtain the corresponding compound of formula I which, if desired, may be reacted with a selective cleavage agent for —COOR to obtain a compound of the formula

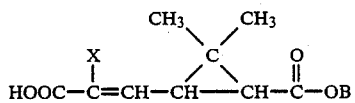

IV and the latter or a functional derivative thereof may be reacted with an alcohol of the formula R—OH wherein R has the above definition to obtain the corresponding compound of formula I.

To prepare a compound of formula I$_A$, a compound of the formula

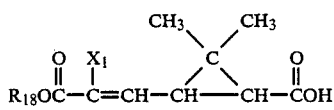

II$_A$ wherein X$_1$ and R$_{18}$ have the above definition in the form of a mixture of its (E) and (Z) isomers or in the (E) form or (Z) form on all of its stereoisomeric forms or mixture thereof or a functional derivative thereof is reacted with an alcohol of the formula

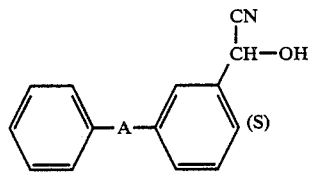

III$_A$ wherein A has the above definition or a functional derivative thereof and optionally separating the (E) and (Z) isomers by physical means.

The esterification of the acid of formulae II or II$_A$ with the alcohol of formulae III or III$_A$ may be effected in the presence of a tertiary base such as pyridine or in the presence of a mixture of pyridine, 4-dimethylaminopyridine and dicyclohexylcarbodiimide. The esterification may also be effected with the acid chloride and the alcohol or a metallic derivative of the alcohol such as its silver salt. The acids of formulae II or II$_A$ may be prepared by the Wittig reaction to obtain the acids with the double bond of the (E) and (Z) geometry which can be separated by physical methods such as chromatography of the acids or their esters.

The selective cleavage agent for the group —COOR preferably is heat used with an acid hydrolysis agent such as p-toluenesulfonic acid. The esterification of the compounds of formula IV may be effected by classical methods.

A process for the preparation of the acids of formulae II or II$_A$ wherein R or R$_{18}$ is alkyl of 1 to 5 carbon atoms comprises reacting by the Wittig reaction in the presence of a strong base a cis aldehyde of the formula

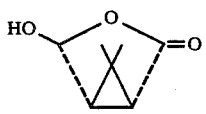

V or a trans aldehyde of the formula

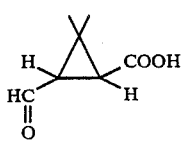

VI with a phosphorane of the formula

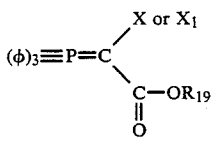

VII wherein X and X$_1$ have the above definitions and R$_{19}$ is alkyl of 1 to 5 carbon atoms or with a phosphonate of the formula

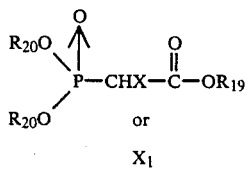

wherein $R_{19}$, X and $X_1$ have the above definitions and $R_{20}$ is alkyl of 1 to 6 carbon atoms.

The acids of formula II with a determined stereochemistry may also be prepared by the following reaction scheme:

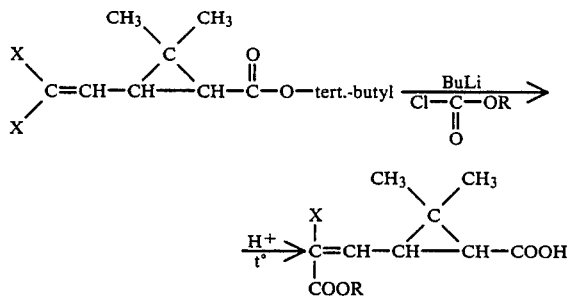

wherein X is fluorine, chlorine or bromine and R is alkyl of 1 to 8 carbon atoms and the starting compounds have a well defined steric configuration.

The acids of formula II wherein X is bromine may also be prepared by reacting a compound of the formula

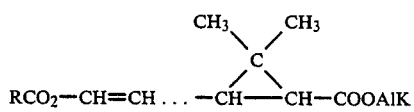

wherein the double bond has the E geometry, Alk is an alkyl and R has the above definition with a bromination agent such as pyridinium tribromide then with a dehydrobrominating agent either under mild conditions such as in the presence of triethylamine to obtain the (Z) isomer of the compound of the formula

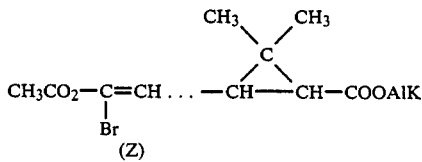

or under stronger conditions such as sodium hydroxide to obtain the corresponding (E) isomer.

The compounds of formula V may be subjected to a selective cleavage agent for the group —COOAlK to obtain the corresponding acid of formula II.

The novel pesticidal compositions of the invention are comprised of a pesticidally effective amount of at least one compound of formula I and an inert carrier. The compositions are useful to combat pests such as parasites of vegetables and of warm-blooded animals as well as parasites of premises and are particularly useful to combat insects, nematodes and parasitic acariens which attack warm-blooded animals and vegetables.

The compositions of the invention are particularly useful to combat insects in the agricultural field, for example, to control aphides and larvae of lepidoptera and coleoptera and are usually used at a dose of 10 to 300 g of the compounds of formula I per hectare. The compositions are also useful to combat insects in the premises for example to combat flies, mosquitoes and beetles.

Among the preferred pesticidal compositions are those containing as the active ingredient (S) 2-methyl-3-(2-propen-1-yl)-4-oxo-2-cyclopenten-1-yl (1R, cis, E) 2,2-dimethyl-3-[2-fluoro-3-oxo-3-methoxy-1-propenyl]-cyclopropanecarboxylate, [3-(2-propyn-1-yl)-2,5-dioxo-1-imidazolidinyl]methyl (1R, cis, E) 2,2-dimethyl-3[2-(fluoro-3-oxo-3-methoxy-1-propenyl]cyclopropanecarboxylate or (S)α-cyano-3-phenoxy-4-fluoro-benzyl (1R, cis, E) 2,2-dimethyl-3-[2-fluoro-3-oxo-3-(1,1-dimethylethoxy)-1-propenyl]-cyclopropanecarboxylate.

Certain of the compounds of formula I possess an excellent lethal power and a very good knock-down power and the products of Examples 1, 11 and 21 are particularly remarkable on this point. The products of formula I have the advantages of being very photostable and not being toxic to mammals. The various properties of the compounds of formula I correspond perfectly to those required for modern agrochemical use permitting the protection of crops without damage to the environment.

The pesticidal compositions of the invention are useful to combat vegetable parasitic acariens and nematodes as well as to combat animal parasitic acariens such as ticks, especially ticks of Boophilus species, Hyalomnia species, Amblyomnia species and Rhipicephalus species and to combat all sorts of scabies such as sarcoptic scabies, psoroptic scabies and chorioptic scabies.

The invention also includes compositions intended to combat parasites of warm-blooded animals, parasites of premises and parasites of vegetables containing at least one compound of formula I, and especially of formula $I_4$.

The invention particularly includes insecticidal compositions containing as active principle, at least one compound of formula I, especially the compounds of Examples 1, 11 and 21.

For the compositions intended for premises or agricultural use, the compositions may also contain one or more other pesticidal agents. The compositions may be in the form of powders, granules, suspensions, emulsions, solutions, aerosol solutions, combustible bands, baits and other preparations classically used for compounds of this type.

Besides the active ingredient, the compositions generally contain a vehicle and/or a nonionic surface active agent to ensure a uniform dispersion of the substances in the mixture. The vehicle used may be a liquid such as water, alcohol, hydrocarbons or other organic solvents or a mineral, animal or vegetable oil or a powder such as talc, clays, silicates or Kieselguhr or a combustible solid. The insecticidal compositions usually contain 0.005 to 10% by weight of the compounds of formula I.

In an advantageous operation for use in premises, the compositions are in the form of fumigants. These compositions advantageously have for thier inactive portion a combustible serpentine or coil base or an incombustible fibrous substrate. In the latter case, the fumigant obtained after incorporation of the active ingredient of formula I is placed in a heating apparatus such as an electromosquitoe destroyer. The usual active dose in this case is 0.03 to 95% by weight, preferably.

In the case of a serpentine insecticide, the inert support may be made, for example, of pyrethrum marc, Tabu powder (or Machilus Thumbergii leaf powder), powder of pyrethrum stems, cedar needle powder, sawdust such as pine sawdust, starch and powder of coconut shells. The active dose in this case is preferably 0.03 to 1% by weight.

The compositions of the invention for premises use may be prepared as a spraying oil containing the active ingredient and the oil may soak the wick of a lamp which is then subjected to combustion. The concentration of the compound of the invention in the oil is preferably 0.03 to 95% by weight.

The insecticidal compositions as well as the acaricidal and nematocidal compositions of the invention may also contain one or more other pesticides and are in the usual powder, granule, suspension, emulsion or solution form. For acaricide use, the compositions are preferably wettable powders for foliar spraying containing 1 to 80% of the active ingredient of liquids for foliar spraying containing 1 to 500 g/l of the active ingredient. Also useful are powders for foliar powdering containing 0.05 to 3% by weight of the active ingredient. For nematocide use, the compositions are in the form of liquids for soil treatment containing 300 to 500 g/l of the active ingredient. For acaricide and nematocide use, the preferred dose of the active compounds is 1 to 100 g per hectare.

To increase the biological activity of the compositions of the invention, classical synergists may be incorporated therein such as 1-(2,5,8-trioxadodecyl)-2-propyl-4,5-methylenedioxy-benzene (piperonyl butoxide) or N-(2-ethyl-heptyl)bicyclo-[2,2-1] 5-heptene-2,3-dicarboximide or piperonyl-bis-2-(2'-n-butoxy-ethoxy)-ethyl acetal (tropital).

When the compositions are to be used to combat parasitic acariens of animals, the active compounds of the invention are very often incorporated into alimentary compositions in association with a nutritive mixture adapted to the animal to be fed. The nutritive mixture will vary depending upon the specific animal but usually contains cereals, sugars and grains, soybean press cake, peanuts and turnsole, meal of animal origin such as fish meal, synthetic amino acids, mineral salts, vitamins and antioxidants.

The compositions of the invention show an excellent general tolerance and are equally useful as medicaments for treating affections created by ticks and scabies. The compositions may be used in veterinary and human medicines. In human medicine, the compositions may be used to combat lice as well as prevent or treat scabies. The compositions may also be used as anthelmintics.

The said medicaments may be administered externally by vaporization, by shampoo, by painting or by bathing. For veterinary usage, the compositions may also be administered by painting the dorsal spine by the "pour on" method as well as being administered digestively or parenterally.

The compositions of the invention are also useful as biocides or to regulate growth.

Another feature of the invention are insecticidal, acaricidal or nematocidal associations containing as an active ingredient at least one compound of formula I and as a second active ingredient at least one pyrethrinoid ester selected from the group consisting of esters of allethrolones, of 3,4,5,6-tetrahydrophthalimido-methyl alcohol, of 5-benzyl-3-furylmethyl alcohol, of 3-phenoxy-benzyl alcohol and α-cyano-3-phenoxy-benzyl alcohols with chrysanthemic acids, esters of 5-benzyl-3-furyl-methyl alcohol with 2,2-dimethyl-3-(2-oxo-3-tetrahydrothiophenylidene methyl)-cyclopropane-1-carboxylic acids, esters of 3-phenoxy-benzyl alcohol and α-cyano-3-phenoxy-benzyl alcohols with 2,2-dimethyl-3-(2,2-dichlorovinyl)-cyclopropane-1-carboxylic acids, esters of α-cyano-3-phenoxy-benzyl alcohols with 2,2-dimethyl-3-(2,2-dibromovinyl)-cyclopropane-1-carboxylic acids, esters of 3-phenoxy-benzyl alcohol with 2p-chlorophenyl-2-isopropyl-acetic acids, esters of allethrolone, 3,4,5,6-tetrahydrophthalimido-methyl alcohol, 5-benzyl-3-furyl-methyl alcohol, 3-phenoxy-benzyl alcohol or α-cyano-3-phenoxy-benzyl alcohols with 2,2-dimethyl-3-(1,2,2,2-tetrahaloethyl)-cyclopropane-1-carboxylic acids where halo is fluorine, chlorine or bromine wherein the compounds of formula I and the above pyrethrinoid esters are in all possible stereoisomer forms.

The latter associated compositions of the invention are of particular interest for combatting by the polyvalence of their action, a large range of parasites or by manifesting a synergistic action in some cases.

The novel method of the invention for combatting parasites such as insects, nematodes and acariens comprises contacting the parasites with a pesticidally effective amount of at least one compound of formula I.

The acids of formulae II or $II_A$ and especially those with a well determined stereochemistry and the compounds of formula IV produced in the process of the invention are novel compounds and are also objects of the invention.

Among the novel intermediate acids of the invention are the E and Z isomers of (1R, cis) 2,2-dimethyl-3-[2-fluoro-3-oxo-3-(1,1-dimethylethoxy)-1-propenyl]-cyclopropane carboxylic acid, the E and Z isomers of (1R, cis) 2,2-dimethyl-3-[2-bromo-3-oxo-3-ethoxy-1-propenyl]-cyclopropane carboxylic acid, (1R, cis, E) 2,2-dimethyl-3-[2-fluoro-3-oxo-3-methoxy-1-propenyl]-cyclopropane carboxylic acid, the E and Z isomers of (1R, cis) 2,2-dimethyl-3-[2-chloro-3-oxo-3-(2-butoxy)-1-propenyl]-cyclopropane carboxylic acid, the E and Z isomers of (1R, cis) 2,2-dimethyl-3-[2-bromo-3-oxo-3-(2-butoxy)-1-propenyl]-cyclopropane carboxylic acid, benzyl (1R, cis, E) 2,2-dimethyl-3-[2-fluoro-3-oxo-3-hydroxy-1-propenyl]-cyclopropane carboxylate, (S)α-cyano-3-phenoxy-4-fluoro-benzyl (1R, cis, E) 2,2-dimethyl-3-[2-fluoro-3-oxo-3-hydroxy-1-propenyl]-cyclopropane carboxylate and the E and Z isomers of (1R, trans) 2,2-dimethyl-3-[2-bromo-3-oxo-3-ethoxy-1-propenyl]-cyclopropane carboxylic acid.

In the following examples there are described several preferred embodiments to illustrate the invention. However, it should be understood that the invention is not intended to be limited to the specific embodiments.

EXAMPLE 1

(S)α-cyano-3-phenoxy-benzyl (1R, cis) 2,2-dimethyl-3(E)-[2-fluoro-2-ethoxycarbonyl-ethenyl]-cyclopropane-1-carboxylate STEP A: (1R, cis) 2,2-dimethyl-3-(E,Z)-[2-fluoro-2-ethoxycarbonyl-ethenyl]-cyclopropane-1-carboxylic acid 2 g of sodium hydride as a 60% oil suspension were added at 5° C. to a solution of 12.1 g of ethyl diethyl-phosphoro fluoroacetate in 120 ml of dimethoxyethane and after stirring the mixture for 30 minutes, 5.7 g of the lactone of (1R, cis) 2,2-dimethyl-3-dihydroxymethylcyclopropane-1-carboxylic acid were added thereto at 0° C. The mixture was stirred at 20° C. for 2½ hours and was then poured into a mixture of ice and water containing monosodium phosphate. The mixture was extracted with ether and the organic phase was washed with water, dried and evaporated to dryness under reduced pressure. The residue was chromatographed over silica gel and was eluted with a 50-50-1 cyclohexane-ethyl acetate-acetic acid mixture to obtain 3.87 g of (1R, cis) 2,2-dimethyl-3-(E,Z)-[2-fluoro-2-ethoxycarbonyl-ethenyl]-cyclopropane-1-carboxylic acid.

STEP B: (S)α-cyano-3-phenoxy-benzyl (1R, cis) 2,2-dimethyl-3-(E)-[2-fluoro-2-ethoxycarbonyl-ethenyl]-cyclopropane-1-carboxylate 1.5 ml of pyridine and 3.7 g of dicyclohexylcarbodiimide were added to a solution of 3.87 g of the product of Step A in 30 ml of methylene chloride and after stirring the mixture for 10 minutes, a solution of 4.05 g of (S)α-cyano-3-phenoxy-benzyl alcohol in 10 ml of methylene chloride was added thereto all at once. The mixture was stirred for 90 minutes and 25 mg of 4-dimethylamino-pyridine were added thereto. The mixture was stirred for 90 minutes and was cooled to 0° C. and was filtered. The filtrate was evaporated to dryness under reduced pressure and the mixture was chromatographed over silica gel. Elution was with a 4-1 cyclohexaneethyl acetate mixture and the residue was crystallized from ethyl acetate and was vacuum filtered. The filtrate was chromatographed over silica gel and elution was with a 9-1 cyclohexane-ethyl acetate mixture to obtain 4.28 g of (S)α-cyano-3-phenoxy-benzyl (1R, cis) 2,2-dimethyl-3-(E)-[2-fluoro-2-ethoxycarbonyl-ethenyl]-cyclopropane-1-carboxylate and 2.8 g of the 3(Z)-isomer.

Analysis: $C_{25}H_{24}NFO_2$; molecular weight=437.47. Calculated: %C, 68.64; %H, 5.53; %N, 3.20; %F, 4.34. Found: 68.8; 5.5; 3.1; 4.2.

IR Spectrum (chloroform):
Absorption at 1738 and 1722 $cm^{-1}$ (carbonyl and conjugated ester); at 1611 $cm^{-1}$ (ethylenic double bond); at 1589–1489 $cm^{-1}$ (aromatic ring); at 1380 $cm^{-1}$ (geminal methyls).

NMR Spectrum (deuterochloroform):
Peaks at 1.2–1.27 ppm (hydrogens of geminal methyls); at 1.23–1.35–1.47 ppm and 4.15–4.26 ppm and 4.38–4.50 ppm (hydrogens of ethyl of ethoxycarbonyl); at 1.88–2.02 ppm (1-hydrogen of cyclopropyl); at 2.8–3.13 ppm (3-hydrogen of cyclopropyl); at 6.05–6.21 and 6.38–6.55 ppm (hydrogen of ethylenic double bond); at 6.36 ppm (hydrogen on carbon attached to —CN; at 6.9–7.58 ppm (aromatic hydrogen).

EXAMPLE 2

(S)α-cyano-3-phenoxy-benzyl (1R, cis) 2,2-dimethyl-3-(Z)-[2-fluoro-2-ethoxycarbonyl-ethenyl]-cyclopropane-1-carboxylate The 2.8 g of (1R, cis) 2,2-dimethyl-3-(Z)-[2-fluoro-2-ethoxycarbonyl-ethenyl]-cyclopropane-1-carboxylic acid of Step A of Example 1 was empasted with ethyl acetate and filtered. The filtrate was evaporated to dryness under reduced pressure and the residue was chromatographed over silica gel. Elution with a 9-1 cyclohexane-ethyl acetate mixture yielded 1 g of (S)α-cyano-3-phenoxy-benzyl (1R, cis) 2,2-dimethyl-3-(Z)-[2-fluoro-2-ethoxycarbonyl-ethenyl]-cyclopropane-1-carboxylate.

IR Spectrum (chloroform):
Absorption at 1730 $cm^{-1}$ (carbonyl+conjugated ester); at 1620 $cm^{-1}$ (ethylenic double bond); at 1589–1489 $cm^{-1}$ (aromatic hydrogens); at 1380 $cm^{-1}$ (geminal methyls).

NMR Spectrum (deuterochloroform):
Peaks at 1.2–1.32–1.43 ppm and 4.12–4.23–4.35–4.47 ppm (hydrogens) of ethyl of ethoxycarbonyl); at 1.23–1.27 ppm (hydrogens of geminal methyls); at 6.2–6.36 ppm and 6.73–6.9 ppm (ethylenic double bond hydrogens); at 6.47 ppm (hydrogen on carbon attached to —CN); at 6.9–7.58 ppm (aromatic hydrogens).

EXAMPLE 3

(S)α-cyano-3-phenoxy-benzyl (1R, cis) 2,2-dimethyl-3(E)-[2-chloro-2-methoxycarbonyl-ethenyl]-cyclopropane-1-carboxylate STEP A: (1R, cis) 2,2-dimethyl-3-(E)-[2-chloro-2-methoxycarbonyl-ethenyl]-cyclopropane-1-carboxylic acid 12.6 g of methoxycarbonyl chloromethylene triphenyl phosphorane were added at 20° C. to 50 ml of tetrahydrofuran and after the addition of a solution of 4.85 g of the lactone of (1R, cis) 2,2-dimethyl-3-dihydroxymethyl-cyclopropane-1-carboxylic acid in 40 ml of tetrahydrofuran to the mixture, it was stirred at 20° C. for 2 hours and then refluxed for one hour. The mixture was evaporated to dryness under reduced pressure and the mixture was added to ether. The mixture was filtered and the filtrate was evaporated to dryness under reduced pressure. The residue was chromatographed over silica gel and was eluted with an 8-2 benzene-ethyl acetate mixture to obtain 2.2 g of (1R, cis) 2,2-dimethyl-3-(E)-[2-chloro-2-methoxycarbonyl-ethenyl]-cyclopropane-1-carboxylic acid and 3 g of the 3(Z) isomer.

IR Spectrum (chloroform):
3(E) isomer: Absorption at 3500 $cm^{-1}$ (—OH of carboxyl); at 1721, 1713 and 1700 $cm^{-1}$ (carbonyl); at 1490–1410 $cm^{-1}$ (C=C); at 1393–1380 $cm^{-1}$ (hydrogens of geminal methyls).

3(Z) isomer: Absorption at 3500 $cm^{-1}$ (monomeric and dimeric —OH of carboxyl); at 1725 $cm^{-1}$ (ester carbonyl); at 1700 $cm^{-1}$ (monomeric hydrogen of carboxyl); at 1623 $cm^{-1}$ (C=C); at 1393–1381 $cm^{-1}$ (hydrogens of geminal methyls).

NMR Spectrum (deuterochloroform):
3(E) isomer: Peaks at 1.3–1.32 ppm (geminal methyls); at 1.87–2.02 ppm (1-hydrogen of cyclopropyl); at 2.82 and 2.97 ppm and 2.98 and 3.13 ppm (3-hydrogen of cyclopropyl); at of tert-butyl (1R, cis) 2,2-dimethyl-3-(2,2-dibromovinyl)-cyclopropane-1-carboxylate in 120 ml of tetrahydrofuran and 120 ml of ether and after stirring the mixture at −115° C. for 15 minutes, 10 ml of n-propyl chloroformate were progressively added thereto. The mixture was stirred at −115° C. for 20 minutes, at −65° C. for one hour and was poured into an aqueous monosodium phosphate solution. The mixture was extracted with ether and the organic phase was washed with water, dried and evaporated to dryness under reduced pressure. The residue was chromatographed over silica gel and was eluted with a 95-5 cyclohexane-ethyl acetate mixture to obtain 3.52 g of tert.-butyl (1R, cis) 2,2-dimethyl-3(Z)-[2-bromo-2-propyloxycarbonylethenyl]-cyclopropane-1-carboxylate and 3.16 g of the corresponding 3(E)-isomer.

IR Spectrum (chloroform): 3(Z) isomer

Absorption at $1715^{cm-1}$ (carbonyl) and at $1614^{cm-1}$ (C=C).

NMR Spectrum (deuterochloroform): 3(Z) isomer

Peaks at 0.9–0.97–1.05 ppm (hydrogens of $CH_3$ — of propyl); at 1.3–1.33 ppm (hydrogens of geminal methyls); at 1.52 ppm (hydrogens of tert.-butyl); at 1.88–1.97 ppm and 2.05–2.15–2.24 ppm (1- and 3-hydrogens of cyclopropyl); at 4.1–4.18–4.26 ppm (hydrogens of 1-methylene of cyclopropyl); at 7.6–7.75 ppm (hydrogen of ethylenic double bond).

STEP B: (1R, cis) 2,2-dimethyl-3(Z)-[2-bromo-2-propoxycarbonylethenyl]-cyclopropane-1-carboxylic acid 0.35 g of p-toluene sulfonic acid monohydrate were added to a solution of 3.45 g of the product of Step C in in 35 ml of toluene and the mixture was placed in a balloon flask in an oil bath at 120° C. for 10 minutes. The temperature was then rapidly cooled to 20° C. and ether was added thereto. The organic phase was washed with water, dried and evaporated to dryness under reduced pressure to obtain 2.9 g of (1R, cis) 2,2-dimethyl-3(Z)-[2-bromo-2-propoxycarbonyl-ethenyl]-cyclopropane-1-carboxylic acid.

STEP C: (S)α-cyano-3-phenoxy-benzyl (1R, cis) 2,2-dimethyl-3(Z)-[2-bromo-2-propoxycarbonyl-ethenyl]-cyclopropane-1-carboxylate 0.9 ml of pyridine and 2.1 g of dicyclohexylcarbodiimide were added to a solution of 2.9 g of the product of Step B in 40 ml of methylene chloride and the mixture was stirred for 15 minutes. A solution of 2.5 g of (S)α-cyano-3-phenoxy-benzyl alcohol in 15 ml of methylene chloride and then 25 mg of 4-dimethylamino-pyridine were added to the reaction mixture which was stirred for 2 hours and filtered. The filtrate was evaporated to dryness under reduced pressure and the residue was chromatographed over silica gel. Elution with a 9-1 cyclohexane-ethyl acetate mixture yielded 4.26 g of (S)α-cyano-3-phenoxy-benzyl (1R, cis) 2,2-dimethyl-3(Z)-[2-bromo-2-propoxycarbonyl-ethenyl]-cyclopropane-1-carboxylate melting at 64° C.

Analysis: $C_{20}H_{26}BrNO_5$; molecular weight=512.41
Calculated: %C, 60.95; %H, 5.11; %N, 2.73; %Br, 15.6.
Found: 61.1; 5.3; 2.7; 15.5.

IR Spectrum (chloroform):

Absorption at $1743-1718^{cm-1}$ (ester carbonyl+conjugated ester); at $1615^{cm-1}$ (C=C); at $1588-1488^{cm-1}$ (aromatic ring) at $1390-1380^{cm-1}$ (geminal methyls).

NMR Spectrum (deuterochloroform):

Peaks at 0.88–1.0–1.12 ppm (hydrogens of methyl of propyl); at 1.27–1.32 ppm (hydrogens of geminal methyls); at 4.08–4.2–4.32 ppm (1-hydrogens of propyl); at 6.4 ppm (hydrogen on carbon attached to —CN); at 7.57–7.67 ppm (hydrogen of ethylenic double bond); at 6.9–7.58 ppm (aromatic hydrogens).

EXAMPLE 5

(S)α-cyano-3-phenoxy-benzyl (1R, cis) 2,2-dimethyl-3(E)-[2-bromo-2-propoxycarbonyl-ethenyl]-cyclopropane-1-carboxylate

STEP A: (1R, cis) 2,2-dimethyl-3(E)-[2-bromo-2-propoxycarbonyl-ethenyl]-cyclopropane-1-carboxylic acid 0.31 g of p-toluene sulfonic acid monohydrate were added to a solution of 3.1 g of tert.-butyl (1R, cis) 2,2-dimethyl-3(E)-[2-bromo-2-propoxycarbonyl-ethenyl]-cyclopropane-1-carboxylic acid obtained by the procedure of Step A of Example 4 in 31 ml of toluene and the mixture was placed in a balloon flask in an oil bath at 120° C. for 15 minutes. The mixture was rapidly cooled to 20° C. and was extracted with ether. The organic phase was washed with water, dried and evaporated to dryness under reduced pressure to obtain 2.6 g of (1R, cis) 2,2-dimethyl-3(E)-[2-bromo-2-propoxycarbonyl-ethenyl]-cyclopropane-1-carboxylic acid.

STEP B: (S)α-cyano-3-phenoxy-benzyl (1R, cis) 2,2-dimethyl-3(E)-[2-bromo-2-propoxycarbonyl-ethenyl]-cyclopropane-1-carboxylate 0.9 ml of pyridine and 2 g of dicyclohexylcarbodiimide were added to a solution of 2.6 g of the product of Step A in 40 ml of methylene chloride and the mixture was stirred for 10 minutes. 2 g of (S)α-cyano-3-phenoxy-benzyl alcohol were added to the mixture which was stirred for 10 minutes after which 25 mg of 4-dimethylamino-pyridine were added thereto. The mixture was stirred for 90 minutes and was filtered and the filtrate was evaporated to dryness under reduced pressure. The residue was chromatographed over silica gel and was eluted with a 95-5 cyclohexane-ethyl acetate mixture to obtain 0.743 g of (S)α-cyano-3-phenoxy-benzyl (1R, cis) 2,2-dimethyl-3(E)-[2-propoxycarbonyl-ethenyl]-cyclopropane-1-carboxylate and 3.64 g of a mixture. The latter was dissolved in 4 volumes of hot isopropyl ether and the mixture was stirred at 20° C. and was then vacuum filtered to obtain another 2.32 g of the desired ester melting at 68° C.

Analysis: $C_{26}H_{23}NBrO_5$; molecular weight=512.41
Calculated: %C, 60.95; %H, 5.11; %N, 2.73; %Br, 15.6.
Found: 61; 5.1; 2.5; 15.5.

IR Spectrum (chloroform):

Absorption at $1737^{cm-1}$ (ester carbonyl); at $1705^{cm-1}$ (conjugated ester carbonyl); at $1605-1610^{cm-1}$ (C=C); at $1585-1485^{cm-1}$ (aromatic ring).

NMR Spectrum (deuterochloroform):

Peaks at 0.88–1.0–1.12 ppm (hydrogens of $CH_3$— of propyl); at 1.22–1.23 ppm (hydrogens of geminal methyls); at 1.92–2.06 ppm (1-hydrogen of cyclopropyl); at 4.08–4.18–4.28 ppm (hydrogens of 1-methylene of propyl); at 6.38 ppm (hydrogen on carbon attached to —CN); at 6.9 to 7.51 ppm (hydrogen of ethylenic double bond); at 6.92–7.6 ppm (aromatic hydrogens).

EXAMPLE 6

(1R,cis) 2,2-dimethyl-3(E)-[2-fluoro-2-ethoxycarbonyl-ethenyl]-cyclopropane-1-carboxylic acid Using the procedure of Example 1, 12.2 g of the lactone of (1R,cis) 2,2-dimethyl-3-dihydroxymethyl-cyclopropane-1-carboxylic acid were reacted to obtain (1R,cis) 2,2-dimethyl-3(E,Z)-[2-fluoro-2-ethoxycarbonyl-ethenyl]-cyclopropane-1-carboxylic acid which was chromatographed over silica gel and was eluted with a 3-1 cyclohexane-ethyl acetate mixture and then with a 1-1 cyclohexane-ethyl acetate mixture to obtain 14.5 g of (1R,cis) 2,2-dimethyl-3(E)-[2-fluoro-2-ethoxycarbonyl-ethenyl]-cyclopropane-1-carboxylic acid with a specific rotation of $[α]_D^{20} = -42.5°$ (c=1% in chloroform). The said acid was esterified with (S)α-cyano-3-phenoxy-benzyl alcohol by the procedure of Example 1.

NMR Spectrum (deuterochloroform):

Peaks at 1.28 ppm (hydrogens of geminal methyls); at 1.23–1.35–1.47 ppm and 4.13–4.25–4.37–4.48 ppm (hydrogens of ethyl of ethoxycarbonyl); at 1.82–1.97 ppm (1-hydrogen of cyclopropyl); at 2.75–2.9–3.05 ppm (3-hydrogen of cyclopropyl); at 6.12–6.28–6.47–6.63 ppm (ethylenic hydrogen —J=21 Hz—corresponds to cis derivative); at 11.28 ppm (carboxyl hydrogen).

EXAMPLE 7

(1R,cis) 2,2-dimethyl-3(Z)-[2-fluoro-2-ethoxycarbonyl-ethenyl]-cyclopropane-1-carboxylic acid Following the chromatography of Example 6, there was obtained 4.64 g of (1R,cis) 2,2-dimethyl-3(Z)-[2-fluoro-2-ethoxycarbonyl-ethenyl]-cyclopropane-1-carboxylic acid. The said acid was esterified with (S)α-cyano-3-phenoxy-benzyl alcohol by the procedure of of Example 2.

EXAMPLE 8

(S)α-cyano-3-phenoxy-benzyl (1R,cis) 2,2-dimethyl-3(Z)-[2-fluoro-2-ethoxycarbonyl-ethenyl]-cyclopropane-1-carboxylate 1.9 ml of pyridine and 4.8 g of dicyclohexylcarbodiimide were added to a solution of 4.9 g of (1R,cis) 2,2-dimethyl-3(Z)-[2-fluoro-2-ethoxycarbonyl-ethenyl]-cyclopropane-1-carboxylic acid in 39 ml of methylene chloride and a solution of 5.3 g of (S)α-cyano-3-phenoxy-benzyl alcohol in 9.8 ml of methylene chloride was added with stirring to the mixture. After stirring the mixture for 2 hours, 30 mg of 4-dimethylamino-pyridine were added thereto and the mixture was stirred for 2 hours. The mixture was cooled to 0° C. and was filtered and the filtrate was evaporated to dryness under reduced pressure. The residue was chromatographed over silica gel and was successively eluted with a 9-1 cyclohexane-ethyl acetate mixture and with a 6-4 methylene chloride-petroleum ether (b.p.=35°-70° C.) mixture to obtain 6.73 g of (S)α-cyano-3-phenoxy-benzyl (1R,cis) 2,2-dimethyl-3(Z)-[2-fluoro-2-ethoxycarbonyl-ethenyl]-cyclopropane-1-carboxylate with the same characteristics of the compound of Example 2.

EXAMPLE 9

Using the procedure of Example 1, (1R,cis) 2,2-dimethyl-3(E)-[2-fluoro-2-ethoxycarbonyl-ethenyl]-cyclopropane-1-carboxylic acid and R [3-ethynyl-3-phenoxy]-benzyl alcohol were reacted to obtain a 72% yield of R-[3-ethynyl-3-phenoxy]-benzyl (1R,cis) 2,2-dimethyl-3(E)-[2-fluoro-2-ethoxy carbonyl-ethenyl]-cyclopropane-1-carboxylate with a specific rotation of $[\alpha]_D^{20} = +40° \pm 1.5°$ (c=1% in chloroform).

EXAMPLE 10

Using the procedure of Example 1, (1R,cis) 2,2-dimethyl-3(E)-[2-fluoro-2-ethoxycarbonyl-ethenyl]-cyclopropane-1-carboxylic acid and (R) 3-phenoxy-phenethyl alcohol were reacted to obtain an 81% yield of (R) 3-phenoxy-phenethyl (1R,cis) 2,2-dimethyl-3(E)-[2-fluoro-2-ethoxycarbonyl-ethenyl]-cyclopropane-1-carboxylate with a specific rotation of $[\alpha]_D^{20} = +94.5° \pm 2.5°$ (c=0.5% in chloroform).

EXAMPLE 11

Using the procedure of Example 1, (1R,cis) 2,2-dimethyl-3(E)-[2-ethoxycarbonyl-ethenyl]-cyclopropane-1-carboxylic acid and (S)α-cyano-3-phenoxy-4-fluoro-benzyl alcohol were reacted to obtain (S)α-cyano-3-phenoxy-4-fluoro-benzyl (1R,cis) 2,2-dimethyl-3(E)-[2-fluoro-2-ethoxycarbonyl-ethenyl]-cyclopropane-1-carboxylate with a specific rotation of $[\alpha]_D^{20} = +50° \pm 2.5°$ (c=0.5% in chloroform).

EXAMPLE 12

Using the procedure of Example 1, (1R,cis) 2,2-dimethyl-3(E)-[2-fluoro-2-ethoxycarbonyl-ethenyl]-cyclopropane-1-carboxylic acid and 3-phenoxy-benzyl alcohol were reacted to obtain 3-phenoxy-benzyl (1R,cis) 2,2-dimethyl-3(E)-[2-fluoro-2-ethoxycarbonyl-ethenyl]-cyclopropane-1-carboxylate.

IR Spectrum (chloroform):

Absorption at $1725^{cm-1}$ (ester carbonyl and conjugated ester carbonyl); at $1655^{cm-1}$ (conjugated C=C); at $1588–1489^{cm-1}$ (aromatic); at $1390–1380^{cm-1}$ (geminal methyls).

EXAMPLE 13

(S)α-cyano-3-phenoxy-benzyl (1R, trans) 2,2-dimethyl-3(E)-[2-fluoro-3-oxo-3-ethoxy-propenyl]-cyclopropane-1-carboxylate

STEP A: (1R, trans) 2,2-dimethyl-3(E)-[2-fluoro-3-oxo-3-ethoxypropenyl]-cyclopropane-1-carboxylic acid A solution of 7.7 g of ethyl diethyl-phosphono-fluoroacetate (prepared by process of Ann. Chem., 1964, p. 6741), 60 ml of 1,2-dimethoxyethane and 4 g of (1R, trans) 2,2-dimethyl-3-formyl-cyclopropane-carboxylic acid was added over 30 minutes at 2° to 10° C. to a suspension of 2.6 g of a 60% sodium hydride in oil suspension and 60 ml of 1,2-dimethoxyethane and the mixture was stirred at 5° C. for 15 minutes, and then at room temperature for 3 hours. The resulting solution was poured into aqueous monosodium phosphate solution at 5° C. and the mixture was stirred for 10 minutes. The mixture was extracted with ethyl acetate and the organic phase was washed with water, dried and evaporated to dryness at 40° C. under reduced pressure to obtain 6.5 g of an oil residue. The latter was chromatographed over silica gel and was eluted with a 70-30-1 hexane-ethyl acetate-acetic acid mixture to obtain 4 g of (1R,trans) 2,2-dimethyl-3(E)-[2-fluoro-3-oxo-3-ethoxy-propenyl]-cyclopropane-1-carboxylic acid

STEP B: (S)α-cyano-3-phenoxy-benzyl (1R, trans) 2,2-dimethyl-3(E)-[2-fluoro-3-oxo-3-ethoxy-propenyl]-cyclopropane-1-carboxylate Using the procedure of Example 1, the product of Step A and (S)α-cyano-3-phenoxy-benzyl alcohol were reacted to obtain (S)-cyano-3-phenoxy-benzyl (1R,trans) 2,2-dimethyl-3(E)-[2-fluoro-3-oxo-3-ethoxy-propenyl]-cyclopropane-1-carboxylate with a specific rotation of $[\alpha]_D^{20} = -33.5° \pm 2.5°$ (c=0.5% in chloroform).

EXAMPLE 14

(S)α-cyano-3phenoxy-benzyl (1R,trans) 2,2-dimethyl-3(E)-[2-fluoro-3-oxo-3-methoxy-propenyl]-cyclopropane-1-carboxylate

STEP A: (S)α-cyano-3-phenoxy-benzyl (1R,trans) 2,2-dimethyl-3(E)-[2-fluoro-3-oxo-3-hydroxy-propenyl]-cyclopropane-1-carboxylate 50 mg of p-toluene sulfonic acid monohydrate were added to a solution of 1 g of the product of Example 13, 1 ml of water and 4 ml of dioxane and the mixture was refluxed for 8 hours and evaporated to dryness at room temperature under reduced pressure. The residue was taken up in methylene chloride and the solution was washed with water, dried and evaporated to dryness to obtain 1.1 g of an oil residue. The latter was chromatographed over silica gel and was eluted with a 60-40-1 hexane-ethyl acetate-acetic acid mixture to obtain 280 mg of (S)α-cyano-3-phenoxy-benzyl (1R,trans) 2,2-dimethyl-3(E)-[2-fluoro-3-oxo-3-hydroxy-propenyl]-cyclopropane-1-carboxylate.

STEP B: (S)α-cyano-3-phenoxy-benzyl (1R, trans) 2,2-dimethyl-3(E)-[2-fluoro-3-oxo-3-methoxy-propenyl)-cyclopropane-1-carboxylate A slight excess of diazomethane in methylene chloride solution was added at 5° to 10° C. to a solution of 860 mg of the product of Step A in 2 ml of methylene chloride and the mixture was stirred at 5° C. for 15 minutes and at room temperature for 30 minutes. A few drops of acetic acid were added to the mixture which was then evaporated to dryness to obtain 950 mg of an oil residue. The latter was chromatographed over silica gel and was eluted with an 85-15 hexane-ethyl acetate mixture to obtain 700 mg of (S)α-cyano-3-phenoxy-benzyl (1R, trans) 2,2-dimethyl-3(E)-[2-fluoro-3-oxo-3-methoxy-propenyl]-cyclopropane-1-carboxylate with a specific rotation of $[\alpha]_D^{20} = -31° \pm 2.5°$ (c=0.25% in chloroform).

EXAMPLE 15

(S)α-cyano-3-phenoxy-benzyl (1R,trans) 2,2-dimethyl-3(Z)-[2-fluoro-3-oxo-3-ethoxy-propenyl]-cyclopropane-1-carboxylate STEP A: (1R,trans) 2,2-dimethyl-3(Z)-[2-fluoro-3-oxo-3-ethoxy-propenyl]-cyclopropane-1-carboxylic acid A solution of 4 g of (1R, trans) 2,2-dimethyl-3-formyl-cyclopropane-1-carboxylic acid and 7 g of the sodium salt of diethyl oxalofluoro acetate was refluxed for one hour and was then allowed to cool to room temperature. The mixture was poured into aqueous saturated monosodium phosphate solution at 0° to 5° C. and the mixture was extracted with ether. The organic phase was washed with water and evaporated to dryness to obtain 8.2 g of residue. The latter was chromatographed over silica gel and was eluted with a 70-30-1 hexane-ethyl acetate-acetic acid mixture to obtain 4.3 g of (1R,trans) 2,2-dimethyl-3(Z)-[2-fluoro-3-oxo-3-ethoxy-propenyl]-cyclopropane-1-carboxylic acid.

STEP B: (S)α-cyano-3-phenoxy-benzyl (1R,trans) 2,2-dimethyl-3(Z)-[2-fluoro-3-oxo-3-ethoxy-propenyl]-cyclopropane-1-carboxylate Using the procedure of Example 1, the acid of Step A and (S)α-cyano-3-phenoxy-benzyl alcohol were reacted to obtain (S)α-cyano-3-phenoxy-benzyl (1R,trans) 2,2-dimethyl-3(Z)-[2-fluoro-3-oxo-3-ethoxy-propenyl]-cyclopropane-1-carboxylate with a specific rotation of $[\alpha]_D^{20} = +15° \pm 2°$ (c=0.5% in chloroform).

EXAMPLE 16

Using the procedure of Step A of Example 14, the product of Example 8 was reacted to form (S)α-cyano-3-phenoxybenzyl (1R,cis) 2,2-dimethyl-3(Z)-[2-fluoro-3-oxo-3-hydroxypropenyl]-cyclopropane-1-carboxylate which then was reacted by the procedure of Step B of Example 14 to obtain (S)α-cyano-3-phenoxy-benzyl (1R,cis) 2,2-dimethyl-3(Z)-[2-fluoro-3-oxo-3-methoxy-propenyl]-cyclopropane-1-carboxylate with a specific rotation of $[\alpha]_D^{20} = -2.5° \pm 2°$ (c=0.4% in chloroform).

EXAMPLE 17

(S)α-cyano-3-phenoxy-benzyl (1R,cis) 2,2-dimethyl-3(Z)-[2-fluoro-3-oxo-3-tert.-butoxy-propenyl]-cyclopropane-1-carboxylate STEP A: tert-butyl N-isopropyl-N'-isopropyl-carbamimidate A mixture of 98.7 g of N,N'-disopropylcarbodiimide, 57.9 g of tert-butanol and 5 g of cuprous chloride was stirred for 4½ days at room temperature to obtain 117.7 g of tert butyl N-isopropyl-N'-isopropyl-carbamimidate after distilling the mixture at 74° C. at 9 mm Hg.

STEP B: (S)α-cyano-3-phenoxy-benzyl (1R,cis) 2,2-dimethyl-3(Z)-[2-fluoro-3oxo-3-tert.-butoxy-propenyl]-cyclopropane-1-carboxylate A mixture of 15 ml of ethyl acetate, 2.4 g of the product of Step A and 2.3 g of (S)α-cyano-3-cyano-3-phenoxybenzyl (1R,cis) 2,2-dimethyl-3(Z)-[2-fluoro-3-oxo-3-hydroxypropenyl]-cyclopropane-1-carboxylate was stirred for 2 hours and was filtered. The filtrate was evaporated to dryness to obtain 2.6 g of residue which was chromatographed over silica gel. Elution with an 8-2 n-hexane-isopropyl ether mixture yielded 2.2 g of product which was crystallized from isopropyl ether to obtain 1.4 g of (S)α-cyano-3-phenoxy-benzyl (1R,cis) 2,2-dimethyl-3(Z)-[2-fluoro-3-oxo-3-tert.-butoxy-propenyl]-cyclopropane-1-carboxylate melting at 103° C. and having a specific rotation of $[\alpha]_D^{20} = +2.5° \pm 3°$ (c=0.2% in chloroform).

EXAMPLE 18

(S)α-cyano-3-phenoxy-benzyl (1R,cis) 2,2-dimethyl-3(Z)-[2-fluoro-3-oxo-3-(1,1,1,3,3,3-hexafluoroisopropoxy)-propenyl]-cyclopropane-1-carboxylate A solution of 0.6 g of dicyclohexylcarbodiimide, 21 mg of 4-dimethylamino-pyridine and 5 ml of methylene chloride was added over 10 minutes at 5° to 10° C. to a solution of 1.1 g of (S)α-cyano-3-phenoxy-benzyl (1R,cis) 2,2-dimethyl-3(Z)-[2-fluoro-3-oxo-3-hydroxypropenyl]-cyclopropane-1-carboxylate, 5 ml of methylene chloride and 0.5 ml of 1,1,1,3,3,3-hexafluoro-isopropanol and the mixture was filtered. The filtrate was evaporated to dryness and the residue was chromatographed over silica gel. Elution with a 9-1 hexane-ethyl acetate mixture yielded 750 mg of (S)α-cyano-3-phenoxybenzyl (1R,cis) 2,2-dimethyl-3(Z)-[2-fluoro-3-oxo-3-(1,1,1,3,3,3-hexafluoroisopropoxy)-propenyl]-cyclopropane-1-carboxylate with a specific rotation of $[\alpha]_D^{20} = +18.5° \pm 1°$ (c=1% in benzene).

EXAMPLE 19

(S)α-cyano-3-phenoxy-benzyl (1R,cis) 2,2-dimethyl-3(E)-[2-fluoro-3-oxo-3-methoxy-propenyl]-cyclopropane-1-carboxylate STEP A: (S)α-cyano-3-phenoxy-benzyl (1R,cis) 2,2-dimethyl-3(E)-[2-fluoro-3-oxo-3-hydroxy-propenyl]-cyclopropane-1-carboxylate A solution of 2.5 g of (S)α-cyano-3-phenoxy-benzyl (1R,cis) 2,2-dimethyl-3(E)-[2-fluoro-3-oxo-3-ethoxypropenyl]-cyclopropane-1-carboxylate, 10 ml of dioxane, 2.5 ml of water and 1 g of p-toluene sulfonic acid manohydrate was refluxed for 24 hours and then allowed to cool to room temperature. Methylene chloride was added to the mixture and the organic phase was washed with water, dried and evaporated to dryness under reduced pressure. The residue was chromatographed over silica gel and was eluted with a 60-40-1 cyclohexane-ethyl acetate-acetic acid mixture to obtain 980 mg of (S)α-cyano-3-phenoxy-benzyl (1R,cis) 2,2-dimethyl-3(E)-[2-fluoro-3-oxo-3-hydroxy-propenyl]-cyclopropane-1-carboxylate.

STEP B: (S)α-cyano-3-phenoxy-benzyl (1R,cis) 2,2-dimethyl-3(E)-[2-fluoro-3-oxo-3-methoxy-propenyl]-cyclopropane-1-carboxylate Using the procedure of Step B of Example 14, the product of Step A was reacted to obtain (S)α-cyano-3-phenoxybenzyl (1R,cis) 2,2-dimethyl-3(E)-[2-fluoro-3-oxo-3-methoxypropenyl]-cyclopropane-1-carboxylate melting at 70° C. and having a specific rotation of $[\alpha]_D^{20} = +52° \pm 1.5°$ (c=1% in chloroform).

EXAMPLE 20

Using the procedure of Example 19, (S)α-cyano-3-phenoxy-benzyl (1R,cis) 2,2-dimethyl-3(E)-[2-fluoro-3-oxo-3-propoxy-propenyl]-cyclopropane-1-carboxylate with a specific rotation of $[\alpha]_D^{20} = +38.5° \pm 2°$ (c=0.7% in chloroform) was prepared.

EXAMPLE 21

Using the procedure of Example 17, (S)α-cyano-3-phenoxy-benzyl (1R,cis) 2,2-dimethyl-3(E)-[2-fluoro-3-oxo-3-hydroxy-propenyl]-cyclopropane-1-carboxylate was reacted to obtain a 61% yield of (S)α-cyano-3-phenoxy-benzyl (1R,cis) 2,2-dimethyl-3(E)-[2-fluoro-3-oxo-3-tert.-butoxy-propenyl]-cyclopropane-1-carboxylate with a specific rotation of $[\alpha]_D^{20} = +26.5°$ (c=0.25% in chloroform).

EXAMPLE 22

Using the procedure of Step B of Example 14, (S)α-cyano-3-phenoxy-benzyl (1R,cis) 2,2-dimethyl-3(E)-[2-fluoro-3-oxo-3-hydroxy-propenyl]-cyclopropane-1-carboxylate and 1,1,1,3,3,3-hexafluoro-isopropanol were reacted to obtain (S)α-cyano-3-phenoxy-benzyl (1R,cis) 2,2-dimethyl-3(E)-[2-fluoro-3-oxo-3-(1,1,1,3,3,3-hexafluoro-isopropoxy)-propenyl]-cyclopropane-1-carboxylate with a specific rotation of $[\alpha]_D^{20} = +21° \pm 2°$ (c=0.5% in chloroform).

EXAMPLE 23

Using the procedure of Example 19, (S)α-cyano-3-phenoxy-benzyl (1R,cis) 2,2-dimethyl-3(E)-[2-fluoro-3-oxo-3-isopropoxy-propenyl]-cyclopropane-1-carboxylate with a specific rotation of $[\alpha]_D^{20} = +46° \pm 1°$ (c=1% in chloroform) was obtained.

EXAMPLE 24

Using the procedure of Example 19, (S)α-cyano-3-phenoxy-benzyl (1R,cis) 2,2-dimethyl-3(E)-[2-fluoro-3-oxo-3-cyclopropoxy-propenyl]-cyclopropane-1-carboxylate with a melting point of 50° C. and a specific rotation of $[\alpha]_D^{20} = +35° \pm 1°$ (c=1.3% in chloroform) was obtained.

EXAMPLE 25

Using the procedure of Example 19, (S)α-cyano-3-phenoxy-benzyl (1R,cis) 2,2-dimethyl-3(E)-[2-fluoro-3-oxo-3-(β-methoxy-ethoxy)-propenyl]-cyclopropane-1-carboxylate with a specific rotation of $[\alpha]_D^{20} = +47° \pm 2.5°$ (c=0.5% in chloroform) was obtained.

EXAMPLE 26

Using the procedure of Step A of Example 14, (S)α-cyano-3-phenoxy-benzyl (1R, trans) 2,2-dimethyl-3(Z)-[2-fluoro-3-oxo-3-ethoxy-propenyl]-cyclopropane-1-carboxylate was reacted to obtain (S)α-cyano-3-phenoxy-benzyl (1R, trans) 2,2-dimethyl-3(Z)-[2-fluoro-3-oxo-3-hydroxy-propenyl]-cyclopropane-1-carboxylate which was reacted by the process of Step B of Example 14 to obtain (S)α-cyano-3-phenoxy-benzyl (1R, trans) 2,2-dimethyl-3(Z)-[2-fluoro-3-oxo-3-methoxypropenyl]-cyclopropane-1-carboxylate with a specific rotation of $[\alpha]_D^{20} = +15.5° \pm 2.5°$ (c=0.3% in chloroform).

EXAMPLE 27

Using the procedure of Example 1, (1R, cis) 2,2-dimethyl-3(Z)-[2-chloro-3-oxo-3-methoxy-propenyl]-cyclopropane-1-carboxylic acid (S)α-cyano-3-phenoxy-benzyl alcohol were reacted to obtain (S)α-cyano-3-phenoxy-benzyl (1R,cis) 2,2-dimethyl-3(Z)-[2-chloro-3-oxo-3-methoxy-propenyl]-cyclopropane-1-carboxylate with a specific rotation of $[\alpha]_D^{20} = +62.5° \pm 1.5°$ (c=1% in benzene).

EXAMPLE 28

(1R,cis) 2,2-dimethyl-3(Z)-[2-chloro-3-oxo-3-methoxy-propenyl]-cyclopropane-1-carboxylic acid chloride and (4S)-hydroxy-3-methyl-2-(2propenyl)-2-cyclopenten-1-one were reacted to obtain (S) 2-methyl-4-oxo-3-(2-propenyl)-2-cyclopenten-1-yl (1R,cis) 2,2-dimethyl-3(Z)-[2-chloro-3-oxo-3-methoxy-propenyl]-cyclopropane-1-carboxylate with a specific rotation of $[\alpha]_D^{20} = -15° \pm 4°$ (c=0.25% in benzene)

NMR Spectrum (deuterochloroform):

Peaks at 1.28 and 1.3 ppm ((hydrogens of geminal methyls); at 3.8 ppm (hydrogens of methyl of —COOCH₃); at 2.02 ppm (hydrogens of methyl of

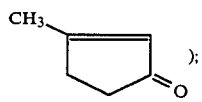

);

at 6.8-7 ppm (ethylenic hydrogen on 1-carbon of 2-methoxycarbonyl-ethenyl).

EXAMPLE 29

(1R,cis) 2,2-dimethyl-3(Z)-[2-chloro-3-oxo-3-methoxypropenyl]-cyclopropane-1-carboxylic acid chloride and (4S) hydroxy-3-methyl-2-(2-propenyl)-2-cyclopenten-1-one were reacted to obtain (1S) 2-methyl-4-oxo-3-(2-propenyl)-2-cyclopenten-1-yl (1R,cis) 2,2-dimethyl-3(Z)-[2-chloro-3-oxo-3-methoxy-propenyl]-cyclopropane-1-carboxylate with a specific $[\alpha]_D^{20} = +27° \pm 2.5°$ (c=0.3% in chloroform).

EXAMPLE 30

(S)α-cyano-3-phenoxy-benzyl (1R,cis) 2,2-dimethyl-3(E)-[2-chloro-3-ethoxy-3-oxo-propenyl]-cyclopropane-1-carboxylate

STEP A:
Ethoxycarbonyl-chloromethylene-triphenyl-phosphorane

A solution of 20 g of ethoxycarbonyl-methylene-triphenyl-phosphorane in 40 ml of chloroform was added at 20° C. to a solution of 4 g of chlorine in 80 ml of chloroform and the temperature was allowed to rise to room temperature. The mixture was evaporated to dryness under reduced pressure and the oil residue was dissolved in 70 ml of methylene chloride. The solution was washed with a solution of 6.1 g of sodium carbonate in 40 ml of water, then with water, dried and evaporated to dryness to obtain 18.9 g of ethoxycarbonyl-chloromethylene-triphenyl-phosphorane melting at 116°–118° C.

STEP B: (1R,cis) 2,2-dimethyl-3(Z,E)-[2-chloro-3-oxo-3-ethoxy-propenyl]-cyclopropane-1-carboxylic acid A solution of 6.9 g of the lactone of (1R,cis) 2,2-dimethyl-3-hydroxymethyl-cyclopropane-1-carboxylic acid in 100 ml of tetrahydrofuran was added to a solution of 18.9 g of the product of Step A in 200 ml of tetrahydrofuran and the mixture was stirred at room temperature for 6½ hours and was evaporated to dryness under reduced pressure. The oil residue was taken up in 50 ml of ether and the mixture was stirred at 0° C. and then was filtered. The filter was washed with ether and the filtrate was evaporated to dryness to obtain 22.2 g of residue. The latter was chromatographed over silica gel and was eluted with a 75-25-1 cyclohexane-ethyl acetate-acetic acid mixture to obtain 3.58 g of (1R,cis) 2,2-dimethyl-3(E)-[2-chloro-3-oxo-3-ethoxy-propenyl]-cyclopropane-1-carboxylic acid and 2.34 g of the corresponding 3(Z)-isomer.

NMR Spectrum (deuterochloroform):

E isomer: Peaks at 1.3 and 1.33 ppm (hydrogens of geminal methyls); at 1.89–2.02 ppm (1-hydrogen of cyclopropyl); at 2.85 to 3.05 ppm (3-hydrogen of cyclopropyl); at 6.78–6.95 ppm (1-hydrogen of propenyl).

Z isomer: Peaks at 1.33 and 1.36 ppm (hydrogens of geminal methyls); at 1.96–2.1 ppm (1-hydrogen of cyclopropyl); at 2.23 to 2.53 ppm (3-hydrogen of cyclopropyl).

STEP C: (S)α-cyano-3-phenoxy-benzyl (1R,cis) 2,2-dimethyl-3(E)-[2-chloro-3-oxo-3-ethoxy-propenyl]-cyclopropane-1-carboxylate Using the procedure of Example 1, the product of Step B and (S)α-cyano-3-phenoxy-benzyl alcohol were reacted to obtain (S)α-cyano-3-phenoxy-benzyl (1R,cis) 2,2-dimethyl-3(E)-[2-chloro-3-oxo-3-ethoxy-propenyl]-cyclopropane-carboxylate with a specific rotation of $[\alpha]_D^{20} = +19° \pm 2°$ (c=1% in chloroform).

EXAMPLE 31

Using the procedure of Example 1, (1R,cis) 2,2-dimethyl-3(Z)-[2-chloro-3-oxo-3-ethoxy-propenyl]-cyclopropane-1-carboxylic acid and (S)α-cyano-3-phenoxy-benzyl alcohol were reacted to obtain (S)α-cyano-3-phenoxybenzyl (1R,cis) 2,2-dimethyl-3(Z)-[2-chloro-3-oxo-3-ethoxy-propenyl]-cyclopropane-1-carboxylate with a specific rotation of $[\alpha]_D^{20} = +21.5° \pm 2.5°$ (c=0.3% in chloroform).

EXAMPLE 32

(S)α-cyano-3-phenoxy-benzyl (1R,cis) 2,2-dimethyl-3(E)-[2-chloro-3-oxo-3-propoxy-propenyl]-cyclopropane-1-carboxylate

STEP A:
Propoxycarbonyl-chloromethylene-triphenyl-phosphorane

Using the procedure of Step A of Example 30, propoxycarbonylmethylene-triphenyl-phosphorane and chlorine were reacted to obtain propoxycarbonyl-chloromethylene-triphenyl-phosphorane.

STEP B: (S)α-cyano-3-phenoxy-benzyl (1R,cis) 2,2-dimethyl-3(E)-[2-chloro-3-oxo-3-propoxy-propenyl]-cyclopropane-1-carboxylate Using the procedure of Step B of Example 30, the product of Step A and the lactone of (1R,cis) 2,2-dimethyl-3-hydroxymethyl-cyclopropane-1-carboxylic acid were reacted to obtain the 3(Z) and 3(E) isomers of (1R,cis) 2,2-dimethyl-3-[2-chloro-3-oxo-3-propoxy-propenyl]-cyclopropane-1-carboxylic acid and the said 3(E) isomer was reacted by the process of Example 1 with (S)α-cyano-3-phenoxy-benzyl alcohol to obtain (S)α-cyano-3-phenoxy-benzyl (1R,cis) 2,2-dimethyl-3(E)-[2-chloro-3-oxo-3-propoxy-propenyl]-cyclopropane-1-carboxylate with a specific rotation of $[\alpha]_D^{20} = +24.5° \pm 2°$ (c=0.4% in chloroform).

EXAMPLE 33

Using the procedure of Example 1, (1R,cis) 2,2-dimethyl-3(Z)-[2-chloro-3-oxo-3-propoxy-1-propenyl]-cyclopropane-1-carboxylic acid and (S)α-cyano-3-phenoxy-benzyl alcohol were reacted to obtain (S)α-cyano-3-phenoxy-benzyl (1R,cis) 2,2-dimethyl-3(Z)-[2-chloro-3-oxo-3-propoxy-propenyl]-cyclopropane-1-carboxylate with a specific rotation of $[\alpha]_D^{20} = +22.5° \pm 2°$ (c=0.7% in chloroform).

EXAMPLE 34

(S)α-cyano-3-phenoxy-benzyl (1R,cis) 2,2-dimethyl-3(E)-[2-chloro-3-oxo-3-tert.-butoxy-propenyl]-cyclopropane-1-carboxylate Using the procedure of Step A of Example 30, tert.-butoxycarbonyl-methylene-triphenyl-phosphorane and chlorine were reacted to obtain tert.-butoxy-chloromethylene-triphenyl-phosphorane melting at =160° C. The said compound and the lactone of (1R,cis) 2,2-dimethyl-3-hydroxymethyl-cyclopropane-1-carboxylic acid were reacted by the procedure of Step B of Example 30 to obtain (1R,cis) 2,2-dimethyl-3(E)-[2-chloro-3-oxo-3-tert.-butoxy-propenyl]-cyclopropane-1-carboxylic acid melting at 65° C. and the corresponding 3(Z)-isomer melting at <50° C.

The said 3(E) isomer was reacted with (S)α-cyano-3-phenyl-benzyl alcohol by the procedure of Example 1 to obtain (S)α-cyano-3-phenoxy-benzyl (1R,cis) 2,2-dimethyl-3(E)-[2-chloro-3-oxo-3-tert.-butoxy-propenyl]-cyclopropane-1-carboxylate with a specific rotation of $[\alpha]_D^{20} = +30.5° \pm 2°$ (c=0.7% in chloroform).

EXAMPLE 35

(S)α-cyano-3-phenoxy-benzyl (1R,cis) 2,2-dimethyl-3(Z)-[2-bromo-3-oxo-3-methoxy-propenyl]-cyclopropane-1-carboxylate STEP A: tert.-butyl (1R,cis) 2,2-dimethyl-3-[1,2-(RS dibromo)-3-oxo-3-methoxy-propyl]-cyclopropane-1-carboxylate 13.3 g of pyridinium tribromide were added to a solution of 8.07 g of tert.-butyl (1R,cis) 2,2-dimethyl-3(E)-[3-oxo-3-methoxy-propenyl]-cyclopropane-1-carboxylate (prepared from the corresponding acid described in EPC published application No. 0018,894) and 50 ml of dimethylsulfoxide and the mixture was stirred for 3½ hours and was then poured into ice water. The mixture was extracted with methylene chloride and the organic phase was dried and evaporated to dryness under reduced pressure to obtain 14.3 g of oil residue. The latter was chromatographed over silica gel and was eluted with a 9-1 hexane-ethyl acetate mixture to obtain 4.3 g of tert.-butyl (1R,cis) 2,2-dimethyl-3-[1,2-(RS dibromo)-3-oxo-3-methoxy-propyl]-cyclopropane-1-carboxylate.

STEP B: Tert.-butyl (1R,cis) 2,2-dimethyl-3(Z)-[2-bromo-3-oxo-3-methoxy-propenyl]-cyclopropane-1-carboxylate 4 ml of triethylamine were added to a solution of 4.2 g of the product of Step A in 40 ml of benzene and the mixture was stirred at 22°-24° C. for 6½ hours and was then diluted with ether. The organic phase was washed with aqueous monosodium phosphate solution, then with water, dried and evaporated to dryness under reduced pressure at 40° C. to obtain 3.3 g of tert.-butyl (1R,cis) 2,2-dimethyl-3(Z)-[2-bromo-3-oxo-3-methoxy-propenyl]-cyclopropane-1-carboxylate.

STEP C: (1R,cis) 2,2-dimethyl-3(Z)-[2-bromo-3-oxo-3-methoxy-propenyl]-cyclopropane-1-carboxylic acid A mixture of 3.3 g of the product of Step B, 30 ml of toluene and 0.33 g of p-toluene sulfonic acid monohydrate was refluxed until gas evolution ceased and was cooled to 20° C. and diluted with ether. The ether phase was washed with water, dried and evaporated to dryness at 40° C. under reduced pressure to obtain 2.9 g of (1R,cis) 2,2-dimethyl-3(Z)-[2-bromo-3-oxo-3-methoxy-propenyl]-cyclopropane-1-carboxylic acid.

STEP D: (S)α-cyano-3-phenoxy-benzyl (1R,cis) 2,2-dimethyl-3(Z)-[2-bromo-3-oxo-3-methoxy-propenyl]-cyclopropane-1-carboxylate Using the procedure of Example 1, the product of Step C and (S)α-cyano-3-phenoxy-benzyl alcohol were reacted to obtain (S)α-cyano-3-phenoxy-benzyl (1R,cis) 2,2-dimethyl-3(Z)-[2-bromo-3-oxo-3-methoxy-propenyl]-cyclopropane-1-carboxylate with a specific rotation of $[\alpha]_D^{20} = +29.5° \pm 2.5°$ (c=0.5% in chloroform).

EXAMPLE 36

(S)α-cyano-3-phenoxy-benzyl (1R,cis) 2,2-dimethyl-3(E)-[2-bromo-3-oxo-3-methoxy-propenyl]-cyclopropane-1-carboxylate STEP A: Tert.-butyl (1R,cis) 2,2-dimethyl-3(E)-[2-bromo-3-oxo-3-methoxy-propenyl]-cyclopropane-1-carboxylate 100 ml of 50% sodium hydroxide solution were added to a mixture of 120 ml of methylene chloride, 6.7 g of tert.-butyl (1R,cis) 2,2-dimethyl-3-[1,2-(RS dibromo-3-oxo-3-methoxy-propyl]-cyclopropane-1-carboxylate and 120 mg of trimethyl cetyl ammonium bromide (Cetavlon) and the mixture was stirred for 4 hours and then diluted with 100 ml of methylene chloride. The organic phase was washed with N hydrochloric acid until the pH of the wash water was 7, dried and evaporated to dryness at 40° C. under reduced pressure to obtain 5.3 g of residue. The latter was chromatographed over silica gel and was eluted with an 8-2 hexane-isopropanol ether mixture to obtain 3.5 g of tert.-butyl (1R,cis) 2,2-dimethyl-3(E)-[2-bromo-3-oxo-3-methoxy-propenyl]-cyclopropane-1-carboxylate.

STEP B: (1R,cis) 2,2-dimethyl-3(E)-[2-bromo-3-oxo-3-methoxy-propenyl]-cyclopropane-1-carboxylic acid A solution of 3.4 g of the product of Step A, 30 ml of toluene, 0.35 g of p-toluene sulfonic acid monohydrate was refluxed until gas evolution ceased and was then cooled to 0° C. and was filtered. The filter was washed with cold toluene and the filtrate was evaporated to dryness at 40° C. under reduced pressure to obtain 2.8 g of (1R,cis) 2,2-dimethyl-3(E)-[2-bromo-3-oxo-3-methoxy-propenyl]-cyclopropane-1-carboxylic acid.

STEP C: (S)α-cyano-3-phenoxy-benzyl (1R,cis) 2,2-dimethyl-3(E)-[2-bromo-3-oxo-3-methoxy-propenyl]-cyclopropane-1-carboxylate Using the procedure of Example 1, the product of Step B and (S)α-cyano-3-phenoxy-benzyl alcohol were reacted to obtain (S)α-cyano-3-phenoxy-benzyl (1R,cis) 2,2-dimethyl-3(E)-[2-bromo3-oxo-3-methoxy-propenyl]-cyclopropane-1-carboxylate with a specific rotation of $[\alpha]_D^{20} = +9.5° \pm 2.5°$ (c=0.3% in chloroform).

EXAMPLE 37

(S)α-cyano-3-phenoxy-benzyl (1R,cis) 2,2-dimethyl-3(E)-[2-bromo-3-oxo-3-tert.-butoxy-propenyl]-cyclopropane-1-carboxylate STEP A: (1R,cis) 2,2-dimethyl-3(E)-[2-bromo-3-oxo-3-tert.-butoxy-propenyl]-cyclopropane-1-carboxylic acid Using the procedure of Step A of Example 30, tert.-butoxycarbonyl-methylene-triphenyl-phosphorane and bromine were reacted to form with tert.-butoxycarbonyl-bromomethylene-triphenyl-phosphorane melting at 190° C. Using the procedure of step B of example 30 the latter was reacted to obtain (1R,cis) 2,2-dimethyl-3(E)-[2-bromo-3-oxo-3-tert.-butoxy-propenyl]-cyclopropane-1-carboxylic acid melting at 76° C. and the corresponding 3(Z)-isomer melting at 50° C.

STEP B: (S)α-cyano-3-phenoxy-benzyl (1R,cis) 2,2-dimethyl-3(E)-[2-bromo-3-oxo-3-tert.-butoxy-propenyl]-cyclopropane-1-carboxylate Using the procedure of Example 1, the product of Step A and (S)α-cyano-3-phenoxy-benzyl alcohol were reacted to obtain (S)α-cyano-3-phenoxy-benzyl (1R,cis) 2,2-dimethyl-3(E)-[2-bromo-3-oxo-3-tert.-butoxy-propenyl]-cyclopropane-1-carboxylate with a specific rotation of $[\alpha]_D^{20} = +16.5° \pm 2°$ (c=0.7% in chloroform).

EXAMPLE 38

Using the process of Example 1, (1R,cis) 2,2-dimethyl-3(Z)-[2-bromo-3-oxo-3-tert.-butoxy-propenyl]-cyclopropane-1-carboxylic acid and (S)α-cyano-3-phenoxy-benzyl alcohol were reacted to obtain (S)α-cyano-3-phenoxy-benzyl (1R,cis) 2,2-dimethyl-3(Z)-[2-bromo-3-oxo-3-tert.-butoxy-propenyl-cyclopropane-1-carboxylate with a specific rotation of $[\alpha]_D^{20} = +16.5° \pm 2°$ (c=0.5% in chloroform).

EXAMPLE 39

(S)α-cyano-3-phenoxy-benzyl (1R,cis) 2,2-dimethyl-3(E)-[2-bromo-3-oxo-3-ethoxy-propenyl]-cyclopropane-1-carboxylate

STEP A: (1R,cis) 2,2-dimethyl-3(E)-[2-bromo-3-oxo-3-ethoxy-propenyl]-cyclopropane-1-carboxylic acid Using the procedure of Step A of Example 30, ethoxy carbonyl-methylene-triphenyl-phosphorane and bromine were reacted to form ethoxycarbonyl-bromomethylene-triphenyl-phosphorane melting at 150° C. which was then reacted with the lactone of (1R,cis) 2,2-dimethyl-3-dihydroxymethyl-cyclopropane-1-carboxylic acid to obtain (1R,cis) 2,2-dimethyl-3(E)-[2-bromo-3-oxo-3-ethoxy-propenyl]-cyclopropane-1-carboxylic acid and the corresponding 3(Z) isomer.

STEP B: (S)α-cyano-3-phenoxy-benzyl (1R,cis) 2,2-dimethyl-3(E)-[2-bromo-3-oxo-3-ethoxy-propenyl]-cyclopropane-1-carboxylate Using the procedure of Example 1, the product of Step A and (S)α-cyano-3-phenoxy-benzyl alcohol were reacted to obtain (S)α-cyano-3-phenoxy-benzyl (1R,cis) 2,2-dimethyl-3(E)-[2-bromo-3-oxo-3-ethoxy-propenyl]-cyclopropane-carboxylate with a specific rotation of $[\alpha]_D^{20} = -70.5° \pm 2°$ (c=0.7% in chloroform).

EXAMPLE 40

Using the procedure of Example 1, (1R,cis) 2,2-dimethyl-3(E)-[2-fluoro-3-oxo-3-ethoxy-propenyl]-cyclopropane-1-carboxylic acid and (RS)α-cyano-6-phenoxy-2-pyridyl-methanol were reacted to obtain (R,S)α-cyano-6-phenoxy-2-pyridyl-methyl (1R,cis) 2,2-dimethyl-3(E)-[2-fluoro-3-oxo-3-ethoxy-propenyl]-cyclopropane-1-carboxylate with a specific rotation of $[\alpha]_D^{20} = +35° \pm 4°$ (c=0.3% in chloroform).

EXAMPLE 41

Using the procedure of Example 1, (1R,cis) 2,2-dimethyl-3(E)-[2-fluoro-3-oxo-3-ethoxy-propenyl]-cyclopropane-1-carboxylic acid and 3-(2-propynyl)-2,5-dioxoimidazolidinyl-methanol were reacted to obtain 3-(2-propynyl)-2,5-dioxoimidazolidinyl-methyl (1R,cis) 2,2-dimethyl-3(E)-[2-fluoro-3-oxo-3-ethoxy-propenyl]-cyclopropane-1-carboxylate with a specific rotation of $[\alpha]_D^{20} = +12° \pm 2°$ (c=0.5% in chloroform).

EXAMPLE 42

Using the procedure of Example 1, (1R,cis) 2,2-dimethyl-3(E)-[2-fluoro-3-oxo-3-ethoxy-propenyl]-cyclopropane-1-carboxylic acid and (S) 2-methyl-3-allyl-4-oxo-2-cyclopenten-1-yl alcohol were reacted to obtain (S) 2-methyl-3-allyl-4-oxo-2-cyclopenten-1-yl (1R,cis) 2,2-dimethyl-3(E)-[2-fluoro-3-oxo-3-ethoxy-propenyl]-cyclopropane-1-carboxylate with a specific rotation of $[\alpha]_D^{20} = +41.5° \pm 2.5°$ (c=0.5% in chloroform).

EXAMPLE 43

3-phenoxy-benzyl (1R,cis,E) 2,2-dimethyl-3-[2-fluoro-3-oxo-3-(1,1-dimethyl-ethoxy)-1-propenyl]-cyclopropane-1-carboxylate

STEP A: (1R,cis,E) 2,2-dimethyl-3-[2-fluoro-3-oxo-3-(1,1-dimethyl-ethoxy)-1-propenyl]-cyclopropane-1-carboxylic acid and its Z isomer A solution of 800 mg of potassium tert.-butylate in 5 ml of tetrahydrofuran was added dropwise to −30° C. to a mixture of 1.2 g of lithium bromide, 600 mg of the internal hemiacetal of 2,2-dimethyl-3-formyl-cyclopropane-1-carboxylic acid, 700 mg of a phosphorofluoroacetate of the formula

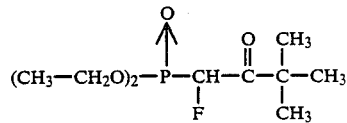

and 20 ml of tetrahydrofuran and after standing at −30° C. for 45 minutes, the mixture was poured into a solution of isopropyl carboxylic acid. The resulting oil was chromatographed over silica gel and eluted with 7--3-0.1 hexane-ethyl acetate-acetic acid mixture to obtain 550 mg of (1R,cis,E) 2,2-dimethyl-3-[2-fluoro-3-oxo-3-(1,1-dimethyl-ethoxy)-1-propenyl]-cyclopropane-1-carboxylic acid and 50 mg of its Z isomer melting at 90° C. after crystallization from hexane.

NMR Spectrum

E isomer—peaks at 1.28 ppm (hydrogens of gem methyls); at 1.55 ppm (hydrogens of tert.-butyl); at 1.81–1.95 ppm (1-hydrogen of cyclopropyl); at 2.73 to 3.05 ppm (3-hydrogen of cyclopropyl); at 6 to 6.5 ppm (1-hydrogen of propenyl).

Z isomer—peaks at 1.28–1.32 ppm (hydrogens of gem methyls); at 1.52 ppm (hydrogens of tert.-butyl); at 1.83–1.97 ppm (1-hydrogen of cyclopropyl); at 2.12 to 2.42 ppm (3-hydrogen of cyclopropyl); at 6.0 to 6.78 ppm (1-hydrogen of propenyl).

STEP B: 3-phenoxy-benzyl (1R,cis,E) 2,2-dimethyl-3[2-fluoro-3-oxo-3-(1,1-dimethylethoxy)-1-propenyl]-cyclopropane-carboxylate 1.76 g of the product of Step A and 10 ml of methylene chloride were added with stirring to a solution of 1.6 ml of 1-chloro-2,N,N-trimethyl-propenylamine and 5 ml of methylene chloride and then 1.6 g of 3-phenoxy-benzyl alcohol, 10 ml of methylene chloride and 2 ml of pyridine were added to the mixture which was then stirred for 16 hours at room temperature and was poured into an aqueous solution of monosodium phosphate. The mixture was stirred until the yellow coloration disappeared and the decanted aqueous phase was extracted with methylene chloride. The combined organic phases were washed with water, dried and evaporated to dryness under reduced pressure. The residue was chromatographed over silica gel and was eluted with a 95-5 hexane-ethyl acetate mixture to obtain 2.1 g of 3-phenoxy-benzyl (1R,cis,E) 2,2-dimethyl-3-[2-fluoro-3-oxo-3-(1,1-dimethylethoxy)-1-propenyl]-cyclopropane-carboxylate with a specific rotation of $[\alpha]_D^{20} = +35° \pm 2°$ (c=0.5% in benzene).

EXAMPLE 44

(R)α-methyl-3-phenoxy-benzyl (1R,cis,E) 2,2-dimethyl-3-[2-fluoro-3-oxo-3-(1,1-dimethyl-ethoxy)-1-propenyl-cyclopropane-carboxylate Using the procedure of Step B of Example 43, the product of Step A of Example 43 and α-methyl-3-phenoxy-benzyl alcohol were reacted to obtain (R)α-methyl-3-phenoxy-benzyl (1R,cis,E) 2,2-dimethyl-3-[2-fluoro-3-oxo-3-(1,1-dimethyl-ethoxy)-1-propenyl]-cyclopropane-carboxylate with a specific rotation of $[\alpha]_D = +137° \pm 5°$ (c=0.2% in benzene).

EXAMPLE 45

(R)α-ethynyl-3-phenoxy-benzyl (1R,cis,E) 2,2-dimethyl-3-[2-fluoro-3-oxo-3-(1,1-dimethyl-ethoxy-1-propenyl]-cyclopropane-carboxylate Using the procedure of Step B of Example 43, the product of Step A of Example 43 and α-ethynyl-3-phenoxy-benzyl alcohol were reacted to obtain (R)α-ethynyl-3-phenoxy-benzyl (1R,cis,E) 2,2-dimethyl-3-[2-fluoro-3-oxo-3-(1,1-dimethyl-ethoxy-1-propenyl]-cyclopropane-carboxylic with a specific rotation of $[\alpha]_D^{20} = +38° \pm 2°$ (c=0.4% in benzene).

EXAMPLE 46

(S)α-cyano-3-phenoxy-4-fluoro-benzyl (1R,cis,E) 2,2-dimethyl-3-[2-chloro-3-oxo-3-(1,1-dimethyl-ethoxy)-1-propenyl]-cyclopropanecarboxylate A mixture of 1.5 g of (1R,cis,E) 2,2-dimethyl-3-[2-chloro-3-oxo-3-(1,1-dimethyl-ethoxy-1-propenyl]-cyclopropane carboxylic acid prepared as in Step B of Example 34 of European Pat. No. 0050534, 1.4 g of (S)α-cyano-3-phenoxy-4-fluorobenzyl alcohol and 20 ml of methylene chloride cooled to 0° C. was admixed with 0.1 g of dimethylamine and then 1.3 g of dicyclohexylcarbodiimide were added thereto. The temperature was allowed to rise to 20° C. and the mixture was stirred at 20° C. for 90 minutes and was then filtered. The filtrate was evaporated to dryness under reduced pressure and the residue was chromatographed over silica gel. Elution with a 9-1 hexane-ethyl acetate mixture yielded 2.05 g of product which was crystallized from isopropyl ether to obtain 1.5 g of (S)α-cyano-3-phenoxy-4-fluoro-benzyl (1R,cis,E) 2,2-dimethyl-3-[2-chloro-3-oxo-3-(1,1-dimethyl-ethoxy)-1-propenyl]-cyclopropanecarboxylate melting at 94° C. and having a specific rotation of $[\alpha]_D^{20} = +35.5° \pm 2.5°$ (c=0.6% in chloroform).

EXAMPLE 47

(S)α-cyano-3-phenoxy-benzyl (1R,cis,Z) 2,2-dimethyl-3-[2-chloro-3-oxo-3-(1,1-dimethylethoxy)-1-propenyl]-cyclopropanecarboxylate (1R,cis,Z) 2,2-dimethyl-3-[2-chloro-3-oxo-3-(1,1-dimethyl-ethoxy)-1-propenyl]-cyclopropane-carboxylic acid prepared as in Step B of Example 34 of European Pat. No. 0050534 and (S)α-cyano-3-phenoxy-benzyl alcohol were reacted to obtain (S)α-cyano-3-phenoxy-benzyl (1R,cis,Z) 2,2-dimethyl-3-[2-chloro-3-oxo-3-(1,1-dimethylethoxy)-1-propenyl]-cyclopropane-carboxylate with a specific rotation of $[\alpha]_D^{20} = +15.5° \pm 1°$ (c=1% in chloroform).

EXAMPLE 48

(S)α-cyano-3-phenoxy-4-fluoro-benzyl (1R,cis,E) 2,2-dimethyl-3-[2-fluoro-3-oxo-3-methoxy-1-propenyl]-cyclopropanecarboxylate Using the procedure of Example 6 of French Pat. No. 2,491,060, the following reaction was effected to obtain (1R,cis,E) 2,2-dimethyl-3-(2-fluoro-3-oxo-3-methoxy-1-propenyl)cyclopropane-carboxylic acid

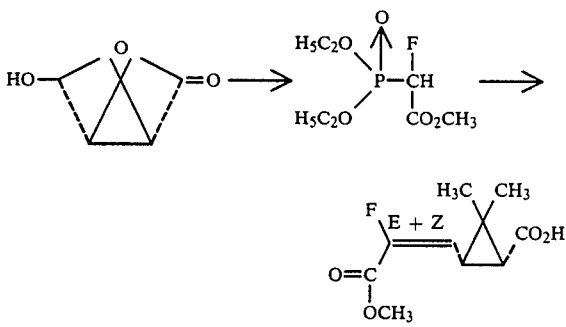

NMR Spectrum (deuterochloroform):

Peaks at 1.3 ppm (hydrogens of geminal methyls); at 1.99-2 ppm (1-hydrogen of cyclopropyl); at 2.75 to 3.08 ppm (3-hydrogen of cyclopropyl); at 3.87 ppm (hydrogens of methoxy); 6.2-6.3 ppm and 6.5-6.7 ppm (ethylenic hydrogen).

The said acid was reacted by the procedure of Step B of Example 43 with (S)α-cyano-3-phenoxy-4-fluoro-benzyl alcohol to obtain (S)α-cyano-3-phenoxy-4-fluoro-benzyl (1R,cis,E) 2,2-dimethyl-3-[2-fluoro-3-oxo-3-methoxy-1-propenyl]-cyclopropanecarboxylate with a specific rotation of $[\alpha]_D^{20} = +46.5° \pm 3°$ (c=0.3% in chloroform).

EXAMPLE 49

Using the procedure of Step B of Example 43, (1R,cis,E) 2,2-dimethyl-3-(2-fluoro-3-oxo-3-methoxy-1-propenyl)-cyclopropane-carboxylic acid and (S) 2-methyl-3-(2-propen-1-yl)-4-oxo-2-cyclopenten-1-ol were reacted to obtain (S)2-methyl-3-(2-propen-1-yl)-4-oxo-2-cyclopenten1-yl (1R,cis,E) 2,2-dimethyl-3-[2-fluoro-3-oxo-3-methoxy-1-propenyl]-cyclopropanecarboxylate with a specific rotation of $[\alpha]_D^{20} = +49.5° \pm 2.5°$ (c=0.3% in chloroform).

EXAMPLE 50

Using the procedure of Step B of Example 43, (1R,cis,E) 2,2-dimethyl-3-[2-fluoro-3-oxo-3-(1,1-dimethyl-ethoxy)-1-propenyl]-cyclopropane carboxylic acid and (S)α-cyano-3-phenoxy-4-fluoro-benzyl alcohol were reacted to obtain (S)α-cyano-3-phenoxy-4-fluoro-benzyl (1R,cis,E) 2,2-dimethyl-3-[2-fluoro-3-oxo-3-(1,1-dimethyl-ethoxy)-1-propenyl]-cyclopropanecarboxylate melting at 122° and having a specific rotation of $[\alpha]_D^{20} = +61° \pm 2.5°$ (c=0.35% in chloroform).

EXAMPLE 51

(S)α-cyano-3-phenoxy-benzyl (1R,cis,E) 2,2-dimethyl-3-(2-fluoro-3-oxo-3-hydroxy-1-propenyl)-cyclopropane carboxylate and 2,2,2-trifluoro-ethanol were reacted to obtain (S)α-cyano-3-phenoxy-benzyl (1R,cis,E) 2,2-dimethyl-3-[2-fluoro-3-oxo-3-(2,2,2-trifluoroethoxy)-1-propenyl]-cyclopropanecarboxylate with a specific rotation of $[\alpha]_D^{20} = +36.5° \pm 2°$ (c=0.5% in chloroform).

EXAMPLE 52

Using the procedure of Step B of Example 34 of European Pat. No. 0050534, the following reaction took place to form the Z and E isomers of (1R,cis) 2,2-dimethyl-3-[2-bromo-3-oxo-3-ethoxy-1-propenyl]-cyclopropane carboxylic acid

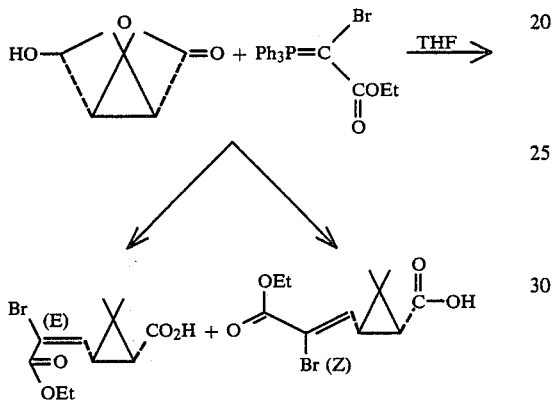

NMR Spectrum (deuterochloroform):

E Isomer: peaks at 1.23–1.35–1.47 ppm and 4.1–4.25–4.36–4.4–8 ppm (hydrogens of ethoxy); at 1.3–1.34 ppm (hydrogens of geminal methyls); at 1.9–2 ppm and 2.8 to 3.1 ppm (1- and 3-hydrogens of cyclopropyl); at 7–7.2 ppm (ethylenic hydrogen); at 9.25 ppm (hydrogen of carboxyl).

Z Isomer: peaks at 1.35 to B 1.4 ppm (hydrogens of geminal methyls); at 1.95 to 2.5 ppm (1- and 3-hydrogens of cyclopropyl); at 7.6 to 7.8 ppm (ethylenic hydrogen); at 8.38 ppm (hydrogen of carboxyl).

The Z isomer of the said acid was reacted by the procedure of Step B of Example 43 with (S)α-cyano-3-phenoxy-benzyl alcohol to obtain (S)α-cyano-3-phenoxy-benzyl (1R,cis,Z) 2,2-dimethyl-3-(2-bromo-3-oxo-3-ethoxy-1-propenyl)-cyclopropane carboxylate with a melting point of 69° C. and specific rotation of $[\alpha]_D^{20} = +25° \pm 2.5°$ (c=0.5% in chloroform).

EXAMPLE 53

Using the procedure of Preparations A and B of Example 30 of European Pat. No. 0050534, the following reaction scheme was followed to obtain the E and Z isomers of (1R,cis) 2,2-dimethyl-3-[2-chloro-3-oxo-3-(1-methyl-propoxy)-1-propenyl]-cyclopropane carboxylic acid

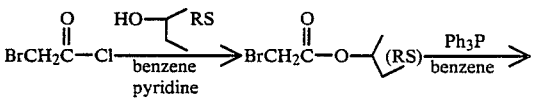

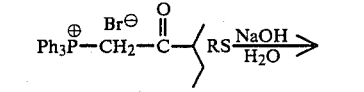

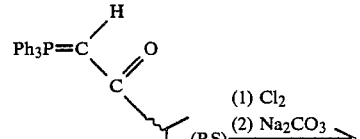

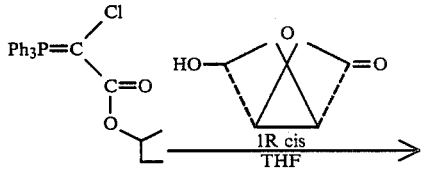

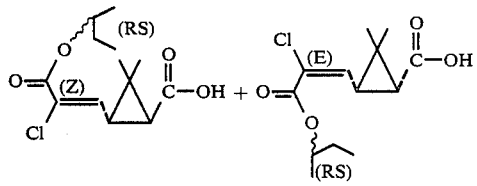

NMR Spectrum (deuterochloroform):

Z isomer: Peaks at 1.23–1.35 ppm (hydrogens of 1-methyl of propoxy); at 0.82–0.93–1.05 ppm (hydrogens of 3-methyl of propoxy); at 1.33 ppm (hydrogens of geminal methyls); at 1.95 to 2.33 ppm (1- and 3-hydrogens of cyclopropyl); at 5 ppm (1-hydrogen of propoxy); at 7.4–7.6 ppm (ethylenic hydrogen).

E isomer: Peaks at 0.8–0.96–1.05 ppm (hydrogens of 3-methyl of propoxy); at 1.27–1.37 ppm (hydrogens of 1-methyl of propoxy); at 1.3–1.33 ppm (hydrogens of geminal methyls); at 1.86–2.0 ppm (1-hydrogen of cyclopropyl); at 2.85 to 3.16 ppm (3-hydrogens of cyclopropyl); at 5 ppm (1-hydrogen of propoxy); at 6.77–6.9 ppm (ethylenic hydrogen).

Using the procedure of Step B of Example 43, the E isomer of the said acid and (S)α-cyano-3-phenoxy-benzyl alcohol were reacted to obtain (S)α-cyano-3-phenoxy-benzyl (1R,cis,E) 2,2-dimethyl-3-[2-chloro-3-oxo-3-(1-methyl-propoxy)-1-propenyl]-cyclopropanecarboxylate with a specific rotation of $[\alpha]_D^{20} = +19° \pm 2.5°$ (c=0.5% in chloroform).

EXAMPLE 54

Using the procedure of Step B of Example 43, (1R,cis,Z) 2,2-dimethyl-3-[2-chloro-3-oxo-3-(1-methyl-propoxy)-1-propenyl]-cyclopropane carboxylic acid and (S)α-cyano-3-phenoxy-benzyl alcohol were reacted to form (S)α-cyano-3-phenoxy-benzyl (1R,cis,Z) 2,2-dimethyl-3-[2-chloro-3-oxo-3-(1-methyl-propoxy)-1-propenyl]-cyclopropanecarboxylate with a specific rotation of $[\alpha]_D^{20} = +16.5° \pm 2°$ (c=0.65% in chloroform).

EXAMPLE 55

Using the procedure of Example 53, the Z and E isomers of (1R,cis) 2,2-dimethyl-3[2-(bromo-3-oxo-3-(1-methylpropoxy)-1-propenyl]-cyclopropane carboxylic acid were prepared and the E isomer was reacted with (S)α-cyano-3-phenoxy-benzyl alcohol by the procedure of Step B of Example 43 to obtain (S)α-cyano-3-phenoxy-benzyl (1R,cis,E) 2,2-dimethyl-3-[2-bromo-3-oxo-3-(1-methylpropoxy)-1-propenyl]-cyclopropanecarboxylate with a specific rotation of $[\alpha]_D^{20} = +8°\pm 1°$ (c=0.5% in chloroform).

EXAMPLE 56

Using the procedure of Step B of Example 43, (1R,cis,Z) 2,2-dimethyl-3-[2-bromo-3-oxo-3-(1-methylpropoxy)-1-propenyl]-cyclopropane carboxylic acid and (S)α-cyano-3-phenoxy-benzyl alcohol were reacted to obtain (S)α-cyano-3-phenoxy-benzyl (1R,cis,Z) 2,2-dimethyl-3-[2-bromo-3-oxo-3-(1-methypropoxy)-1-propenyl]-cyclopropanecarboxylate with a melting point of 76° C. and a specific rotation of $[\alpha]_D^{20} = +21.5°\pm 2°$ (c=0.7% in chloroform).

EXAMPLE 57

Using the procedure of Step B of Example 43, (1R,cis,E) 2,2-dimethyl-3-[2-fluoro-3-oxo-3-(2,2,2-trifluoroethoxy)-1-propenyl]-cyclopropane carboxylic acid and (S)α-cyano-3-phenoxy-4-fluoro-benzyl alcohol were reacted to obtain (S)α-cyano-3-phenoxy-4-fluoro-benzyl (1R,cis,E) 2,2-dimethyl-3-[2-fluoro-3-oxo-3-(2,2,2-trifluoroethoxy)-1-propenyl]-cyclopropanecarboxylate melting at 85° C. and having a specific rotation of $[\alpha]_D^{20} = +43°\pm 2.5°$ (c=0.65% in chloroform).

EXAMPLE 58

Using the procedure of Examples 6 and 7 of French patent No. 2,491,060, the E and Z isomers of (1R, cis) 2,2-dimethyl-3-(2-fluoro-3-oxo-3-ethoxy-1-propenyl)-cyclopropanecarboxylic acid were formed and the Z isomer was reacted with [3-(propyn-2-yl)-2,5-dioxo-1-imidazolidinyl]-methanol to obtain [3-(propyn-2-yl)-2,5-dioxo-1-imidazolidinyl]-methyl (1R, cis, Z) 2,2-dimethyl-3-(2-fluoro-3-oxo-3-ethoxy-1-propenyl)-cyclopropanecarboxylate.

EXAMPLE 59

Using the procedure of Step B of Example 43, (1R, cis, Z) 2,2-dimethyl-3-(2-fluoro-3-oxo-3-ethoxy-1-propenyl)-cyclopropane carboxylic acid and (S) 2-methyl-3-(2-propen-1-yl)-4-oxo-2-cyclopenten-1-yl alcohol were reacted to obtain (S) 2-methyl-3-(2-propen-1-yl)-4-oxo-2-cyclopenten-1-yl (1R, cis, Z) 2,2-dimethyl-3-(2-fluoro-3-oxo-3-ethoxy-1-propenyl)-cyclopropanecarboxylate with a specific rotation of $[\alpha]_D^{20} = +9.5°\pm 2°$ (c=0.5% in chloroform).

EXAMPLE 60

Using the procedure of Example 15 of EPC application Ser. No. 0050534, (1R, trans) 2,2-dimethyl-3-formyl-cyclopropane-carboxylic acid and bromine were reacted to obtain (1R, trans, E) 2,2-dimethyl-3-(2-bromo-3-oxo-3-ethoxy-1-propenyl)-cyclopropane carboxylic acid which was reacted by the procedure of Step B of Example 43 with (S) α-cyano-3-phenoxy-benzyl alcohol to obtain (S)α-cyano-3-phenoxy-benzyl (1R, trans, E) 2,2-dimethyl-3-(2-bromo-3-oxo-3-ethoxy-1-propenyl)-cyclopropanecarboxylate with a specific rotation of $[\alpha]_D^{20} = +20°\pm 1°$ (c=1% in chloroform).

EXAMPLE 61

Using the procedure of Step B of Example 43, (1R, trans, Z) 2,2-dimethyl-3-(2-bromo-3-oxo-3-ethoxy-1-propenyl)-cyclopropane carboxylic acid and (S)-α-cyano-3-phenoxy-benzyl alcohol were reacted to obtain (S) α-cyano-3-phenoxy-benzyl (1R, trans, Z) 2,2-dimethyl-3-(2-bromo-3-oxo-3-ethoxy-1-propenyl)-cyclopropanecarboxylate melting at 97° C. and having a specific rotation of $[\alpha]_D^{20} = +5°\pm 1°$ (c=1% in chloroform).

EXAMPLE 62

Using the procedure of Step B of Example 43, (1R, cis, E) 2,2-dimethyl-3-(2-fluoro-3-oxo-3-methoxy-1-propenyl)-cyclopropane carboxylic acid and [3-(2-propyn-1-yl)-2,5-dioxo-1-imidazolidinyl]-methanol were reacted to obtain [3-(2-propyn-1-yl)-2,5-dioxo-1-imidazolidinyl]-methyl (1R, cis, E) 2,2-dimethyl-3-[2-fluoro-3-oxo-3-methoxy-1-propenyl]-cyclopropanecarboxylate with a specific rotation of $[\alpha]_D^{20} = +3.5°\pm 2°$ (c=0.5% in chloroform).

EXAMPLE 63

11.69 g of benzyl (1R, cis, E) 2,2-dimethyl-3[2-fluoro-3-oxo-3-(1,1-dimethyl-ethoxy-1-propenyl]-cyclopropanecarboxylate prepared from the corresponding acid and benzyl alcohol were added to a solution of 50 ml of toluene and 0.47 g of p-toluene sulfonic acid and the mixture was refluxed for 2½ hours and was then evaporated to dryness under reduced pressure to obtain 10.62 g of an oil. The latter was chromatographed over silica gel and eluted with a 70-30-0.5 hexane-ethyl acetate-acetic acid mixture to obtain 9.65 g of benzyl (1R, cis, E) 2,2-dimethyl-3-[2-fluoro-3-oxo-3-hydroxy-1-propenyl]-cyclopropanecarboxylate melting at 88° C. which was then reacted with ethanol to obtain benzyl (1R, cis, E) 2,2-dimethyl-3-[2-fluoro-3-oxo-3-ethoxy-1-propenyl]-cyclopropanecarboxylate with a specific rotation of $[\alpha]_D^{20} = +32°\pm 2°$ (c=0.5% in chloroform).

EXAMPLE 64

Using the procedure of Example 63, there was obtained benzyl (1R, cis, Z) 2,2-dimethyl-3-[2-fluoro-3-oxo-3-ethoxy-1-propenyl]-cyclopropanecarboxylate with a specific rotation of $[\alpha]_D^{20} = -31°$ (c=0.5% in chloroform).

EXAMPLE 65

Using the procedure of Example 43, there was obtained pentafluorobenzyl (1R, cis, E) 2,2-dimethyl-3-[2-fluoro-3-oxo-3-ethoxy-1-propenyl]-cyclopropanecarboxylate with a specific rotation of $[\alpha]_D^{20} = +16.5°\pm 2°$ (c=0.5% in chloroform).

EXAMPLE 66

Using the procedure of Example 43, there was obtained 4-fluoro-benzyl (1R, cis, E) 2,2-dimethyl-3-[2-fluoro-3-ethoxy-1-propenyl]-cyclopropanecarboxylate with a specific rotation of $[\alpha]_D^{20} = +32°$ (c=3% in chloroform).

EXAMPLE 67

Using the procedure of Example 43, there was obtained 4-fluoro-benzyl (1R, cis, Z) 2,2-dimethyl-3-[2-fluoro-3-oxo-3-ethoxy-1-propenyl]-cyclopropanecarboxylate with a specific rotation of $[\alpha]_D^{20} = -27°$ (c=2.5% in chloroform).

EXAMPLE 68

Using the procedure of Example 43, there was obtained pentafluoro-benzyl (1R, cis, Z) 2,2-dimethyl-3-[2-fluoro-3-oxo-3-(1,1-dimethylethoxy)-1-propenyl]- cyclopropanecarboxylate with a specific rotation of $[\alpha]_D^{20} = -35°$ (c=1% in chloroform).

EXAMPLE 69

Using the procedure of Example 43, there was obtained pentafluorobenzyl (1R, cis, E) 2,2-dimethyl-3-[2-fluoro-3-oxo-3-(1,1-dimethylethoxy)-1-propenyl]-cyclopropanecarboxylate with a specific rotation of $[\alpha]_D^{20} = +25.5°$ (c=1.2% in chloroform).

EXAMPLE 70

Using the procedure of Example 43, there was obtained benzyl (1R, cis, Z) 2,2-dimethyl-3-[2-fluoro-3-oxo-3-(1,1-dimethylethoxy)-1-propenyl]-cyclopropanecarboxylate with a specific rotation of $[\alpha]_D^{20} = -34°$ (c=1.5% in chloroform).

EXAMPLE 71

Using the procedure of Example 43, there was obtained benzyl (1R, cis, E) 2,2-dimethyl-3-[2-fluoro-3-oxo-3-(1,1-dimethylethoxy)-1-propenyl]-cyclopropanecarboxylate with a specific rotation of $[\alpha]_D^{20} = +46.5° \pm 1.5°$ (c=1% in chloroform).

EXAMPLE 72

Using the procedure of Example 43, there was obtained pentafluorobenzyl (1R, cis, E) 2,2-dimethyl-3-[2-fluoro-3-oxo-3-methoxy-1-propenyl]-cyclopropanecarboxylate with a specific rotation of $[\alpha]_D^{20} = +15°$ (c=1% in chloroform).

EXAMPLE 73

Using the procedure of Example 43, there was obtained α-cyano-benzyl (1R, cis, E) 2,2-dimethyl-3-[2-fluoro-3-oxo-3-ethoxy-1-propenyl]-cyclopropanecarboxylate with a specific rotation of $[\alpha]_D^{20} = +37.5°$ (c=1% in chloroform).

EXAMPLE 74

Using the procedure of Example 43, there was obtained benzyl (1R, cis, E) 2,2-dimethyl-3-[2-fluoro-3-oxo-3-methoxy-1-propenyl]-cyclopropanecarboxylate with a specific rotation of $[\alpha]_D^{20} = +35.5°$ (c=1.5% in chloroform).

EXAMPLE 75

Vinyl acetate and (1R, cis, E) 2,2-dimethyl-3-[2-fluoro-3-oxo-3-hydroxy-1-propenyl]-cyclopropane carboxylic acid were reacted in the presence of mercuric acetate as a catalyst to obtain (1R, cis, E) 2,2-dimethyl-3-[2-fluoro-3-oxo-3-ethenyloxy-1-propenyl]-cyclopropane carboxylic acid which was reacted with benzyl alcohol to obtain benzyl (1R, cis, E) 2,2-dimethyl-3-[2-fluoro-3-oxo-3-ethenyloxy-1-propenyl]-cyclopropanecarboxylate with a specific rotation of $[\alpha]_D^{20} = +26°$ (c=1.2% in chloroform).

EXAMPLE 76

Using the procedure of Example 43, there was obtained 4-nitrobenzyl (1R, cis, Z) 2,2-dimethyl-3-[2-fluoro-3-oxo-3-ethoxy-1-propenyl]-cyclopropanecarboxylate with a specific rotation of $[\alpha]_D^{20} = -22.5° \pm 0.5°$ (c=1.5% in chloroform).

EXAMPLE 77

Using the procedure of Example 43, there was obtained 4-nitrobenzyl (1R, cis, E) 2,2-dimethyl-3-[2-fluoro-3-oxo-3-ethoxy-1-propenyl]-cyclopropanecarboxylate with a specific rotation of $[\alpha]_D^{20} = +37° \pm 1.5°$ (c=1.2% in chloroform).

EXAMPLE 78

Using the procedure of Example 43, there was obtained α-phenyl-ethyl (1R, cis, Z) 2,2-dimethyl-3-[2-fluoro-3-oxo-3-ethoxy-1-propenyl]-cyclopropanecarboxylate with a specific rotation of $[\alpha]_D^{20} = -22° \pm 1°$ (c=1% in chloroform).

EXAMPLE 79

Using the procedure of Example 43, there was obtained α-phenyl-ethyl (1R, cis, E) 2,2-dimethyl-3-[2-fluoro-3-oxo-3-ethoxy-1-propenyl]-cyclopropanecarboxylate with a specific rotation of $[\alpha]_D^{20} = +41.5° \pm 1.5°$ (c=1% in chloroform).

EXAMPLE 80

Using the procedure of Example 43, there was obtained ethynylbenzyl (1R, cis, E) 2,2-dimethyl-3-[2-fluoro-3-oxo-3-ethoxy-1-propenyl]-cyclopropanecarboxylate with a specific rotation of $[\alpha]_D^{20} = +30.5° \pm 1.5°$ (c=1% in chloroform).

EXAMPLE 81

Using the procedure of Example 43, there was obtained benzyl (1R, cis, E) 2,2-dimethyl-3-[2-fluoro-3-oxo-3-(1,1-ditrifluoromethyl)methoxy)-1-propenyl]-cyclopropanecarboxylate with a specific rotation of $[\alpha]_D^{20} = +14.5°$ (c=1.5% in chloroform).

EXAMPLE 82

Using the procedure of Example 43, there was obtained benzyl (1R, cis, E) 2,2-dimethyl-3-[2-fluoro-3-oxo-3-(2,2,2-trifluoroethoxy)-1-propenyl]-cyclopropanecarboxylate with a specific rotation of $[\alpha]_D^{20} = +24° \pm 1.5°$ (c=1% in chloroform).

EXAMPLE 83

Using the procedure of Example 43, there was obtained benzyl (1R, cis, E) 2,2-dimethyl-3-[2-fluoro-3-oxo-3-(2,2-difluoroethoxy)-1-propenyl]-cyclopropanecarboxylate with a specific rotation of $[\alpha]_D^{20} = +28.5° \pm 0.5°$ (c=2% in chloroform).

EXAMPLE 84

Using the procedure of Example 43, there was obtained benzyl (1R, cis, E) 2,2-dimethyl-3-[2-fluoro-3-oxo-3-(2-fluoroethoxy)-1-propenyl]-cyclopropanecarboxylate with a specific rotation of $[\alpha]_D^{20} = +28° \pm 0.5°$ (c=2% in chloroform).

EXAMPLE 85

Using the procedure of Example 43, there was obtained pentafluorobenzyl (1R, cis, Z) 2,2-dimethyl-3-[2-fluoro-3-oxo-3-ethoxy-1-propenyl]-cyclopropanecarboxylate with a specific rotation of $[\alpha]_D^{20} = -34°$ (c=1% in chloroform).

PREPARATION A (S) α-cyano-3-phenoxy-4-fluoro-benzyl (1R, cis, E) 2,2-dimethyl-3-[2-fluoro-3-oxo-3-hydroxy-1-propenyl]-cyclopropanecarboxylate was prepared by the process of Example 11 of European Patent Application Ser. No. 0050534 with p-toluene sulfonic acid in refluxing toluene.

NMR Spectrum (deuterochloroform):

Peaks at 1.2–1.27 ppm (hydrogens of geminal methyls); at 1.9–2.0 ppm (1-hydrogen of cyclopropane); at 2.78 to 3.1 ppm (3-hydrogen of cyclopropane); at 6.25–6.42 ppm and 6.58–6.75 ppm (ethylenic hydrogen); at 6.38 ppm (hydrogen on carbon attached to —CN); at 7 to 7.6 ppm (aromatic hydrogens).

PREPARATION B (S) α-cyano-3-phenoxy-benzyl (1R, cis, E) 2,2-dimethyl-3-[2-fluoro-3-oxo-3-hydroxy-1-propenyl]-cyclopropanecarboxylate was prepared by the process of Step A of Example 19 of European Patent Application Ser. No. 0050534.

EXAMPLE 86

A soluble concentrate was prepared by homogenously mixing 0.25 g of the product of Example 1 or Example 50, 1.00 g of piperonyl butoxide, 0.25 g of Tween 80, 0.1 g of Topanol A and 98.4 g of water.

An emulsifiable concentrate was prepared by intimately mixing 0.015 g of the product of Example 11 or Example 62, 0.5 g of piperonyl butoxide, 0.1 g of Topanol A, 3.5 g of Tween 80 and 95.885 g of xylene.

Another emulsifiable concentrate was prepared by homogenously mixing 1.5 g of the product of Example 21 or Example 49, 20,00 g of Tween 80, 0.1 g of Topanol A and 78.4 g of xylene.

A fumigant composition was prepared by homogenously mixing 0.25 g of the product of Example 1 or Example 50, 25 g of tabu powder, 40.00 g of powdered cedar needles, 33.75 g of powdered pine sawdust, 0.5 g of brilliant verte and 0.5 g of p-nitrophenol.

EXAMPLE 87

A pharmaceutical solution was prepared containing 5.00 g of the compound of Example 11, 25.00 g of piperonyl butoxide, 10.00 g of Polysorbate 80, 25.00 g of Triton X 100, 1 g of Tocopherol acetate and sufficient ethanol for a final volume of 100 ml.

Another pharmaceutical solution was prepared containing 0.5 g of product of Example 11, 2.5 g of piperonyl butoxide, 10 g of Polysorbate 80, 25 g of Triton X 100, 1 g of Tocopherol acetate and sufficient ethanol for a final volume of 100 ml.

These solutions are diluted extemporaneously into 5.1 of water.

Pharmaceutical capsules were prepared containing 1 g of the product of Example 1.

EXAMPLE 88

A balanced animal aliment was prepared with a feed base of corn, dehydrated alfalfa, wheat stalks, palm oil molasses press cake, urea and mineral vitamin condiment. The feed contained a minimum of 11% of raw protein material (2.8 % brought from urea), 2.5% of grass material and a maximum of 15% of cellulose material, 6% of mineral material and 13% moisture. The feed corresponded to 82 forage units per 100 kilos and contained per 100 kilos 910,000 International units of vitamin A, 91,000 IU of vitamin $D_3$, 150 mg of vitamin E and 150 mg of vitamin C and the feed contained 0.3 kg of the compound of Example 3 per 100 kg of the total feed.

The same feed base was admixed with 0.04 kg of the compound of Example 1 per 100 kg.

INSECTICIDAL STUDY

The insecticidal activity was determined for (S)α-cyano-3-phenoxy-benzyl (1R, cis) 2,2-dimethyl-3(E)-[2-chloro-3-oxo-3-methoxy-propenyl]-cyclopropane-1-carboxylate (Compound A), (S)α-cyano-3-phenoxy-benzyl (1R, cis) 2,2-dimethyl-3(E)-[2-bromo-3-oxo-3-propoxy-propenyl]-cyclopropane-1-carboxylate (Compound B), (S)α-cyano-3-phenoxy-benzyl (1R, cis) 2,2-dimethyl-3(Z)-[2-bromo-3-oxo-3-propoxy-propenyl]-cyclopropane-1-carboxylate (Compound C) (S)α-cyano-3-phenoxybenzyl (1R, cis) 2,2-dimethyl-3(E)-[2-fluoro-3-oxo-3-ethoxypropenyl]-cyclopropane-1-carboxylate (Compound D), and (S)α-cyano-3-phenoxy-4-fluoro-benzyl (1R, cis, E) 2,2-dimethyl-3-[2-fluoro-3-oxo-3-(1,1-dimethyl-ethoxy)-1-propenyl]-cyclopropane carboxylate (compound of example 50).

A. Lethal effect on houseflies

The test insects were female houseflies of strain sensitive to pyrethrinoids, bred at 22°–23° C. and 60 to 65% relative humidity and 4 to 5 days old. One μl of an acetone solution of the test compound was topically applied to the dorsal thorax of the insects with an Arnold micro-manipulator using 50 insects for each dose. The number of dead was determined 24 hours later and the compounds A, B and the compound of Example 50 had a $DL_{50}$ of 11.1, 1.0 and 0.649 ng per individual, respectively.

B. Lethal effect on Beetles

The tests were effected by contact with a film on glass depositing with a pipette an acetone solution of different concentrations on the bottom of a glass Petri dish of which edges were first impregnated with talc to avoid escape by the insects. The lethal concentration which killed 50% of the insects was determined to be 1.4, 0.40 and 0.034 mg/m² for Compounds A, B and the Compound of Example 50, respectively.

C. Lethal effect on *Spodoptera littoralis*

The test was effected by a topical application of an acetone solution of the test compound with an Arnold micromanipulator to the dorsal thorax of larvae of *Spodoptera littoralis* in the 4th larvae stage using 15 insects per dose. The larvae were 10 days old having been kept at 24° C. and a 65% relative humidity and the larvae, after treatment, were placed in an artificial nutritive medium (Poitout media) and the number of dead was determined after 48 hours. Compounds A, B and C had a $DL_{50}$ of 6.7, 3.2 and 1.0 ng per individual, respectively.

D. Lethal effect on *Epilachna varivestris*

The tests were effected by topical application in an analogous manner to test C with larvae of *Epilachna varivestris* in the last before one larvae stage. After treatment, the larvae were fed bean plant leaves and the number of dead were determined 72 hours after treatment. Compounds A, B and D had $DL_{50}$ of 17.7, 7.4 and 0.85 ng per insect, respectively.

E. Lethal effect on *Aphis Cracivora*

7 day old Adult *Aphis Cracivora* were subjected to a contact-ingestion by treatment with a Fisher pistol on bean leaves placed upon a moist paper disk in a Petri dish made of plastic. The treatment was effected with 2 ml of an acetone solution of the test compound at a rate of 1 ml per leaf surface and after drying of the leaves, they were infested with the insects which were then kept in contact with the leaf for one hour. The insects were placed on untreated leaves and the number of dead insects was determined after 24 hours. Compound B had a DL$_{50}$ of 6.4 ng per insect.

F. Knockdown effect on houseflies 50 female houseflies 4 days old were directly sprayed in a Kearns and March chamber with 0.25 g/l of the test compound in a mixture of Isopar L (petroleum solvent) and 5% acetone at a rate of 2 ml per second. Checkings were taken every minute for 10 minutes and then after 15 minutes to determine the KT$_{50}$ by the usual method. The KT$_{50}$ was 3.6, 4.5, 4.5, and 2.1 and 4.857 minutes for compounds A, B, C, D and the compound of Example 50 respectively.

Using the procedure of test A above, the test compounds were topically applied to the thorax of *Acanthecelides obtectus* in 1 μl of an acetone solution and the DL$_{50}$ was determined to be 6.1 ng per insect for the compound of Example 50.

The above tests show that the compounds have an interesting insecticidal activity and generally the compounds of the invention are endowed with insecticidal activity.

ACARICIDAL ACTIVITY

A. Bean plants containing two leaves were infested with 25 female *Tetranychus Urticae* per leaf and placed with good ventilation in a hood under a constant luminous ceiling. The plants were treated with a Fisher pistol with 4 ml per plant of a toxic solution of 5 g of test compound per hl in equal parts of water and acetone. The plants were dried for 12 hours and then were infested. The number of dead were determined 80 hours later and Compounds A, B and C showed a good acaricidal activity The acaricidal activity against *Tetranychus urticae* was determined on bean leaves and the acaricidal activity against *Panonichus citri* was determined on lemon-tree leaves by spraying both sides of detached leaves which petiole was kept in water, with 2 ml of a 1-1 water-acetone mixture of the test compound. After drying, the leaves were infested with 15 young females per leaf face or 30 females per dose of the test product. 5 doses for the product ranging from 250 to 5000 mg/hl were used. The degree of activity of the products were determined by counting 3 days later. The tests were effected in constant artifical light at about 2000 lux and a temperature of 22°±1° C. and a relative humidity of 60°±5°.

The lethal effect was determined from the number of dead acariens and the repulsion effect was determined from the number of acariens found living outside the leaf. The total effect was the sum of the lethal effect and the respulsive effect and corresponds to the total efficacy of the product. The minimal dose to obtain about 99% total efficacy in 3 days was <250 mg/hl for the compound of Example 50 in both cases.

Various modifications of the compounds and methods of the invention may be made without departing from the spirit or scope thereof and it is to be understood that the invention is intended to be limited only as defined in the appended claims.

What we claim is:

1. A compound having a formula selected from the group consisting of

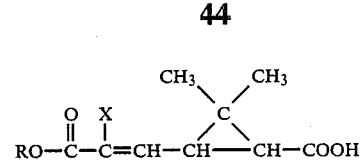

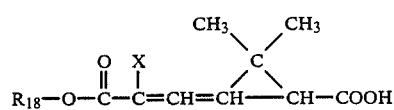

and

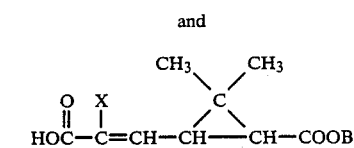

wherein R is selected from the group consisting of (a) alkyl of 1 to 8 carbon atoms of 1 to 8 carbon atoms, alkenyl and alkynyl of 2 to 8 carbon atoms and alkyl of 1 to 8 carbon atoms, alkenyl and alkynyl of 2 to 8 carbon atoms and cycloalkyl of 3 to 8 carbon atoms and cycloalkyl or cycloalkylalkyl of 3 to 8 carbon atoms substituted with at least one member of the group consisting of halogen —OH, —SH, —OR', —SR', —NO$_2$,

—CN, —SO$_3$H, —PO$_4$H$_2$,

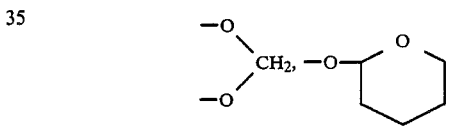

COAlK$_1$, —SO$_2$AlK$_2$, —SO$_3$AlK$_3$, aryl and aryl substituted with at least one member of the group consisting of —OH, alkoxy of 1 to 8 carbon atoms, alkyl of 1 to 8 carbon atoms, halogen, —CF$_3$, —OCF$_3$, —SCF$_3$ and

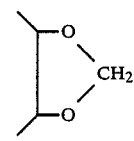

R' is alkyl of 1 to 8 carbon atoms, R" and R''' are individually selected from the group consisting of hydrogen and alkyl of 1 to 8 carbon atoms, AlK$_1$, AlK$_2$ and AlK$_3$ are individually alkyl of 1 to 18 carbon atoms (b) aryl of 6 to 14 carbon atoms and aryl of 6 to 14 carbon atoms substituted with at least one substituent selected from the group consisting of —OH, alkoxy of 1 to 8 carbon atoms, alkyl of 1 to 8 carbon atoms, halogen, —OCF$_3$, —CF$_3$ and —SCF$_3$ and (c) heterocycle selected from the group consisting of pyridinyl, furanyl, thiophenyl, oxazolyl and thiazolyl (d) pyridinyl, furanyl, thiophenyl oxazolyl and thiazolyl, all substituted with at least one member of the group consisting of —OH, alkoxy of 1 to 8 carbon atoms, alkyl of 1 to 8 carbon atoms, halogen, —CF$_3$, —OCF$_3$ and —SCF$_3$, B is selected from the group consisting of alkyl of 1 to 18 carbon atoms, alkenyl and alkynyl of 2 to 8 carbon atoms, cycloalkyl of 3 to 18 carbon atoms, X is halogen, $R_{18}$ is alkyl of 1 to 18 carbon atoms, $X_1$ is fluorine, chlorine or bromine and the ethylenic double bond has the E geometry and the cyclopropane moiety has the (1R, cis) structure.

2. A compound of claim 1 selected from the group consisting of E isomer of (1R, cis) 2,2-dimethyl-3-[2-fluoro-3-oxo-3-(1,1-dimethylethoxy)-1-propenyl]-cyclopropane carboxylic acid, the E isomer of (1R, cis) 2,2-dimethyl-3-[2-bromo-3-oxo-3-ethoxy-1-propenyl]-cyclopropane carboxylic acid, (1R, cis, E) 2,2-dimethyl-3-[2-fluoro-3-oxo-3-methoxy-1-propenyl]-cyclopropane carboxylic acid, the E isomer of (1R, cis) 2,2-dimethyl-3-[2-chloro-3-oxo-3-(2-butoxy)-1-propenyl]-cyclopropane carboxylic acid, the E isomer of (1R, cis) 2,2-dimethyl-3-[2-bromo-3-oxo-3-(2-butoxy)-1-propenyl]-cyclopropane carboxylic acid, benzyl (1R, cis, E) 2,2-dimethyl-3-[2-fluoro-3-oxo-3-hydroxy-1-propenyl]-cyclopropane carboxylic acid, (S)-cyano-3-phenoxy-4-fluoro-benzyl (1R, cis, E) 2,2-dimethyl-3-[2-fluoro-3-oxo-3-hydroxy-1-propenyl]-cyclopropane carboxylate and the E isomer of (1R, trans) 2,2-dimethyl-3-[2-bromo-3-oxo-3-ethoxy-1-propenyl]-cyclopropane carboxylic acid.

* * * * *